(12) United States Patent
Baehrecke

(10) Patent No.: US 7,033,767 B2
(45) Date of Patent: Apr. 25, 2006

(54) GENES REGULATING PROGRAMMED CELL DEATH

(75) Inventor: Eric H. Baehrecke, University Park, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 368 days.

(21) Appl. No.: 10/016,768

(22) Filed: Oct. 29, 2001

(65) Prior Publication Data

US 2002/0142443 A1    Oct. 3, 2002

Related U.S. Application Data

(60) Provisional application No. 60/243,865, filed on Oct. 27, 2000.

(51) Int. Cl.
*G01N 33/53* (2006.01)
(52) U.S. Cl. .................. 435/7.1; 530/350; 530/387.1; 424/181.1; 424/185.1
(58) Field of Classification Search ................ 530/350, 530/300, 387.1; 514/2; 424/9.1, 181.1, 424/185.1; 435/7.1
See application file for complete search history.

(56) References Cited

OTHER PUBLICATIONS

Yuan, J et al, 2003, Neuron, 40: 404-413.*
Wyllie, Ah et al, 1980, Internatl Rev cytology, 68: 251-306.*
Bowie et al (Science, 1990, 257 : 1306-1310).*
Burgess et al (J of Cell Biol. 111:2129-2138, 1990).*
Lazar et al (Molecular and Cellular Biology, 1988, 8:1247-1252).*
Bork (Genome Research, 2000, 10:398-400).*
Scott et al (Nature Genetics, 1999, 21:440-443).*
Oltvai et al, 1994, Cell, 79: 189-192.*
Plasterer, T, N, 2000, Mol Biotech, 16: 117-125.*
Gottschalk, AR et al, 1996, Cell Death and Differentiation, 3(1): 113-118.*
Vogel MW et al, 2002, Cerbellum, 1(4): 277-87.*
Xu Xin et al, 2001, FASEB J, 15(4): A313.*
Hummler E et al, 1994, PNAS, USA, 91: 5647-5661.*
Drexler et al (Leukemia and Lymphoma, 1993, 9:1-25).*
Embleton et al (Immunol Ser, 1984, 23:181-207).*
Hsu (in Tissue Culture Methods and Applications, Kruse and Patterson, Eds, 1973, Academic Press, NY, see abstract, p. 764.*
Freshney (Culture of Animal Cells, A Manual of Basic Technique, Alan R. Liss, Inc., 1983, New York, p4).*
Dermer (Bio/Technology, 1994, 12:320).*
Schimmer, AD, 2003, Cancer Res, 63(6): 1242-8.*
Adams MD, et al, 2000, Genbank Sequence Database (Accession Q9VD60), and MPSRCH search report, 2003, us-10-016-768a-1.rsspt, p.1-2.*

Mahoney et al, 1999, Proceed Natl Acad Sci USA, 96(8): 4536-4539.*
Jackowski et al, 1995, British J Neurosurgery, 1995, 9: 303-317.*
Straub P et al, 1993, J Biol Chem 268(29): 21997-20003.*
Kouklis PD et al, 1993, J Cell Science, 106(pt 3): 919-28.*
Assemat, K et al, 1995. Protein Science, 4 : 2510-2516.*
Kimmel et al.(J. Neurosurg, 66:161-171, 1987).*
Colussi, PA et al, 1998, J Biol Chem, 273(41): 26566-26570.*
Gura (Science, 1997, 278:1041-1042).*
Jain (Sci. Am., 1994, 271:58-65).*
Curti (Crit. Rev. in Oncology/Hematology, 1993, 14:29-39).*
Hartwell et al (Science, 1997, 278:1064-1068).*
Adams, J.M. and Cory, S. (1998). The Bcl-2 protein family arbiter of cell survival. Science 281, 1322-1326.
Baehrecke, E.H. and Thummel, C.S. (1995). The Drosophila E93 gene from the 93F early puff display stage and tissue specific regulation by 20-hydroxyecdysone. Dev. Biol. 171, 85-97.
Cyrns, V. and Yuan, J. (1998). Proteases to die for. Genes Dev. 12, 1551-1570.
Ellis, R.E., et al. (1991). Mechanisms and functions of cell death. Ann. Rev. Cell Bio. 7, 663-698.
Haining, W.N., Carboy-Newcomb, C., Wei, C.L., and Steller, H. (1999). The proapoptotic function of Drosophila Hid is conserved in mammalian cell. Proc. Natl. Acad. Sci. USA 96, 4936-4941.
Lee, C. Y., and Baehrecke, E.H. (2001__. Steroid regulation of autophagic programmed cell death during development. Development 128, 1443-1445.
Lee, C. Y., Wendel, D.P., Reid, P., Lam, G., Thummel, C.S. and Baehrecke, E.H. (2000). E93 directs steroid triggered programmed cell death in Drosphila. Mol. Cell 6, 433-443.
McCarthy, J.C. and Dixit, V.M. (1998). Apoptosis induced by Drosophila Reaper and Grim in a human system. J. Biol. Chem. 273, 24009-24015.
Swiss-Prot database, Swiss institute for Bioinformatics, Geneva, Switzerland, Accession No: Q9VD60.

* cited by examiner

*Primary Examiner*—Susan Ungar
*Assistant Examiner*—Minh-Tam Davis
(74) *Attorney, Agent, or Firm*—Marianne Fuierer; Steven J. Hultquist

(57) ABSTRACT

The present invention to amino acid sequences of proteins that are associated with apoptosis and the use of these proteins in the diagnosis, prevention and treatment of disorders associated with abnormal cell proliferation and apoptosis. The invention relates as well to nucleotide sequences encoding the peptides, recombinant vectors carrying the sequences, recombinant host cells including either the sequences or vectors, and recombinant peptides. The invention further includes methods for using the nucleotide sequences and recombinant peptides in diagnostic and therapeutic applications.

5 Claims, 10 Drawing Sheets

```
human  1  KQPRKKRGRYRQYDHILVEEA.IAMVMSGKMSVSKAQGIYGVPHSTLEYKVKER
fish   1  KQPRKKRGRYRQYDHDLLEEAS.ITMVMAGRMSVSKAQGMYGTPHSTLEYKVKER
mouse  1  KHPRKKRGRYRQYNSILEE.PISMLMSGKMSVSKAQSIYGIPHSTLEYKVKER
fly    1  KGTRPKRGKYRNYDRDSLVEA.VKAVQRGEMSVHRAGSYYGVPHSTLEYKVKER
worm   1  KRSRPKKRGQYRKYDKNALDEA.VRSVRRGEMTVHRAGSFFGVPHSTLEYKVKER
```

```
CGGAGCCCTCGGTGCGCGGCGGAGAGAAGAGGATTCCGGCGGGAACTCGACT
CTTGGCGCCACCGCCTCATGCACTGTGTAGCTCAGTACTAAAACATCAAGTG
GGAGAAAACAAGGGTTTTGAGAGTATTTTAGAAGGGCTTTATGGACCACGGC
TACGAAGAGACCTCAGTTTATTTGAAGACTGTGAACCAGAAGAGCTGACTGA
CTGGTCTATGGATGAAAAATGTTCATTTTGTAACCTACAGAGAGAAGCAGTC
AGTGATTGTATACCATCTCTTGATTCTTCACAGTCAACACCAACAGAGGAGC
TATCATCTCAGGGCCAGTCCAACACTGATAAGATTGAATGCCAAGCAGAAAA
TTACCTAAATGCACTCTTTCGAAAGAAAGCTGATTCAAGCATCTGGGTCTCC
AAGAGGTCTCCTACCAATGGTTGGATCTTCCTCAGAACTGTGATCCTAACAT
TCCCCTAGTTGCTCAGGAATTAATGAAAAGATGATACGTCAATTTGCGATT
GAGTACATTTCAAAAAGTGGTAAAACTCAAGAGAATAGAAATGGTTCAATTG
GACCAAGTATAGTATGTAAAAGTATCCAAATGAATCAAGCAGAAAACTCCCT
TCAGGAAGAGCAGGAAGGCCCCTTAGACCTCACTGTGAATCGAATGCAAGAA
CAAAATACTCAGCAAGGGGATGGAGTGTTAGATCTCTCTACAAAGAAAACCA
GCATAAAATCTGAAGAGTCATCCATATGTGATCCTTCTTCTGAAAATTCAGT
GGCTGGGAGACTACACAGAAACAGAGAGGACTATGTGGAAAGAAGTGCTGAG
TTTGCAGATGGTTTGCTCTCAAAAGCTTTGAAAGACATTCAGTCTGGAGCAC
TGGACATAAATAAAGCAGGCATACTTTATGGCATACCTCAAAAAACTTTACT
TCTTCACTTAGAAGCCTTACCAGCAGGGAAGCCTGCATCTTTTAAAAACAAA
ACTCGAGATTTCCATGATAGTTATTCATATAAGGACAGTAAAGAAACTTGTG
CAGTGCTGCAAAAAGTAGCCTTGTGGGCAAGAGCTCAAGCAGAGCGCACAGA
AAAAGTAAACTCAATCTACTTGAAACCTCAGAAATAAAATTCCCAACAGCT
TCCACTTACCTCCATCAGCTAACTCTACAGAAAATGGTCACTCAGTTTAAAG
AAAAAAATGAAAGCCTCCAATATGAAACTTCAAATCCTACTGTACAGTTAAA
AATTCCTCAGCTACGAGTAAGTTCTGTCTCAAAATCACAACCTGATGGTTCT
GGTCTGTTGGATGTTATGTATCAAGTTTCCAAAACCTCTTCAGTCCTAGAAG
GATCAGCTCTCCAAAAACTGAAAAATATACTCCCTAAACAGAACAAAATAGA
ATGTTCTGGGCCTGTAACTCACTCAAGTGTTGACTCTTACTTTCTACATGGG
GACCTCTCTCCTTTGTGTCTTAATTCTAAAAATGGAACAGTTGATGGAACCT
CTGAAAATACTGAAGATGGATTAGATCGAAAAGACAGTAAGCAGCCCAGGAA
AAAACGTGGCCGCTATCGGCAATATGATCATGAAATAATGGAAGAAGCTATT
GCAATGGTAATGAGCGGAAAAATGAGTGTTTCCAAAGCACAAGGAATTTATG
GGGTACCTCACAGCACTTTAGAATACAAGGTAAAAGAAGATCTGGAACACT
GAAGACTCCTCCGAAGAAGAAACTACGATTACCAGACACTGGGTTATATAAT
ATGACAGATTCAGGGACTGGCAGCTGCAAAAACAGCAGCAAGCCTGTGTAGA
TTACTTGTTAGGAAATGTTTGTGAGTGTGTGTGTGTGTGTGTGTTTGCG
TGTGTGTGTATGTGCACAGGTGTGTATTTGTGTGTCTATATACACACGTGGG
AATTACAAATGCTCACTCTGACAGGAGACATGAAATTTTACAGTTCAAAAAC
CACTTACATGCCTTTTGAAAAAAGTTTTATTCAGGGTTTTCACTGTGGACA
```

Figure 2 A Cont.

```
GAATTATATAGTTGCTTACTTAATTCTGATAGTTTGTATTTAATCCTTGTAT
AAATAGGTGAAAAAGATTCAGGTTTTCTTTAGTAGTCAATAGCATAAAGCGT
TGTGGGAAAACGAGTAATTGTCAAGTGAAACATTTTTATTGGTGAAAGACCA
TTCCAGCCATTCAGTTGAACCATCTTATAATGGAAATATGATATTCATAGTT
TATAAACATTCTATACAACAGACTTAACACTTGTTGTATGTATGTCAAGCAA
CCAATCAAAGTTTAAATAGCTATCTCCATACTAAGAAAAATTAATATATACA
GTATTAGTACACGACAGTGCATTCTATGAAATACAAAATGCACTCAAGTGCA
TCCACCAGGAATAGAAAAGAAAACCTTAAAGGATATGTATAATGAAATTTAA
TATTTATCATTTAATAGTTGATTTAGCAAGAAGTTGGGGTTTATAAGGTATA
TACTTTAAAAAAACTGACACATAGTTAACCCCAGCAGCTATAGAACCCTTTA
ATATAATAAGATGGAGTACTAAGAACAAAAATAATTTAAATTTAATTATTA
AAATAATTTAGTTTTGTTTTTCATTTGAAAAATAAGCTAATGTGTAAGGTTA
GAAAAGAAAGTTGGAATGCAACTTAGAGCATGTTTATAATGTGCACAGAAAA
AGCTTGAGAATGATAATTTTGGTTTAAATGTGCTGGTTAGTTGATGTTATGA
CTACTTTAAATTTTAAGGATTGTGACACACTCCTACTATTGAAAAACCTCAG
TGTAACTTTAATATATTTGCTGCTGTGACATTTCAAAACATTTTCAGTTTAT
CAAAATGAATTGCAGATTTCATTTTGGTGGGCGATACATTATCATTTTGCTA
ATAACCAAATTTGCAGTTTGTTCAGGGTCTTGAATAGATTTACAAATATTTA
ACACTGAAGCTGTTTTGAACTTTCAGTAATGTAAACTCTCTACTAATTGGGT
AGTTAGAAGCTGGGCAGTGCATTTTAACTTTTACTAGACTCATAAGAGAGAC
TGGTCATTTTTACCTAGCAGTTTTAAAATATGGGTCAAAGTATCCTTGTTGG
ATTTATGGAGTATGCAACTGTAGTGGTAAAATGTTATAAAGCATATGCCTTC
ATATAAAGAATAGGGATTTGCTTTATGTATTCCAAAATTCTCTGAGTGCCCC
CTTTCTCCTGTTAAAATTCAGGTTCTGATCATTTTTTCTAAGCCAGTTTTCC
TAAGGTCCAAAAGGAATACTTTTAGCTGAATTTAAAAAATAAGTGCACCTTG
TCAAATGCTTGTGTTTTACACTTGTGTTTGTGTGTATTTAATAATCATATA
TACGTGTAATACTAAAGAGATTTTCAGCTATTAAATTTTAAAACTGCTTACA
TGTTTAAAGAAACTGAAGAGTGAGAAACTACACAACCAAGCAGTTATTTGGT
CTCTGAGATCTATACTTAACCCTCTTCAGCTATTAATGTTACCTGCACACTA
GGGTATGAATCCTCTTTTTTTTTTTTTTTCACCCCAAGAAAATATACATAATA
GATTACAGAACAGCAGATGTCAGGGTCATCTTTCTTTTTAAAGAATTAAGCC
ATATTTTGTGAGGGCCAGAACTTGCATTATTTAGTATATTTCCCCCTTCCCC
CAATGGAAAGCAAAGTTAAAGGTAAAGTACATATTTCAAAACAATTTTATTG
ACCTCTTTATACAGAATTTTACTTGGAAAACTTTGGGGGCTTTGAATGCATT
ACATAATATTTATATTGTATTGAGCTTTTTTATTCCTCACACTATATTTACA
TTAATAAATTGATTGAGAAGTTTATAGTAAAGGGAAACTTACAGAACACTTT
TGTATCATTTAAAAGATGACCTGACCAAAAACTTTACAGGATTCATAAATCA
GGGATCATTTTGCTATTGACTTCACAGTAATCAGTAGTTTTATAGGTAATAT
TATAGTTAATTTGCAGCATTTTAGTACTTGTATTATTTATTTTTGGTCAGAA
```

Figure 2 A cont.

```
ATAGTAAATTAAAATATTTTTTGATAGTTTATAGGTAATAATCAACCCATAA
CTTTTAAAAGAAACAAAACATTTCTATTATTGAGTTAACATTTGATTATACA
AACTAGGAAAGGCAGGGAAATTCCCCTTCTCCCCAGTGATTCTATTAAGATG
ACCTTTATGTTAAACTTTCAAAGTACTTTATGAATTTAGTTACCAGTTACTA
TTTATTAATTGACAATTTTCTGAAAAATCCCGTTTCAGCAGACTTAATGAAG
GTGAAAGCAACCCTTATGTGCTTTCTACTTATTTGAATGTTCCTCAAGTATT
TTATATTAAAAAAAAAAAGAAGGAAAAGAGAAAACAGTGCCTCTGTTTTTAG
AAAACTACTGCTCAGTAAAGTTGTTTAAACCATTTCTGGTAGCTAATGACAA
TTTTATATTAAATTGTATACTAACTTTAGTGAGACTGATTTTTTTAGTTGTT
TACAGTACAAATACTTGTATTTGTTTTTTAATTGCAGTATTTCCAATGTCGC
AGTAATTTAGTAAAACTCTGTGGCTGCCTTGATTTTGACAGATTTTGTTAAT
ATAAACTGATTGTTAGGCAATTAGTTATATTTATGCATAAATCAATTGCACT
ATAATTCATGAATTATTTATTACAATATTTTCTAATGAATTCATGTATCTGT
CTTGTGTTGTAAATGTACTGTAATTCTGTTCCTACTTTGTTGTTATATAT
CTAAATCTGATTGTATGAATTTTAATTGTTCAGTTAACGTGTTTCTAGGTTG
TAATTTGTAGTAAAGCACTTCAATGCTTTTGCACTTAAATTTACAACACTGT
TGGTGTGTGATTGATTTACTCATTCAGTAAAAGAAAAAAAGAAAAGCAAAAG
GAAAAAAAAAAAAAAAAA
```

Figure 2 B

```
CTACATTGTGTTCTGAGTGGGGCTGATGAGTTAGATTTGGTGAGAATTAGGA
GGGGTTGCCGGGGTGAGGCGGGGGTCAGGAGGAGAAGAGTATGAATCTTCTA
GGCAGAGGAAACCAATTCCAAGTGTGAAAGCCCAGAAACGAGAAATAGCATA
GCACTTTCCCAGCAGGTTTCCCTGCTCCACCTTTAGCTCCTTGCGGTCCATT
CTCCCATAGCAGATTGATCTTTTAAAAACCTAAATTGAAATCATGTCAGTCT
TCCACCCAGAATTCTCCAGTGGCTTCCTGTCTCTGTCAGAATGAAATGCGAA
GTTCTTGCCATGGCCCAATGGCCCTGTTTAACCTCTTCCTATAACATTTCTG
ATCTCAGCTCACTCTTGGCCTGGCTTCCTTCATTTCAGATACCCTGGCCTTT
GCTATTCCTCTGACATTCCAGACATGGTTCCATATCACAGCCCCTATACAGA
CTGTTCTTTTGGAAACGTTCTCCCATGTATCTGATTAGTTGGTGATCCTCAC
CTTATTCAGGGCCCTGTTCAAATCAAAGAAGCCTGCACTGATAACACTGTGT
AAAACAGCAGCATTCTCAGCCCCACCCTCATTACTCTATCAGCTTACTCTGT
GTTATTTTCCAGGGTGGCACTATCATAATTGCTGGTGGTAGTGGTGCTGGTT
GTGGTGTTGTATGAATTATCTCATTAGATCCTAAGCACTATGACTATGACAA
TAGGTACTTTGTATGACTTTTTTTTTTGATGCTCTTCTAGTGCCTAAAATAG
TGCTTTGCATATAGTGAGCGCTCAATAAATTATTGTCGAAGTCTATATAGGA
GGCTATAGATAGGATGTTTTGTTTTATTTTTCATCTTTGTATCTGCCCAGGA
ACATACATATTTCATGGATTGATTATGGTTACAGTAAAACCCAGTTGAATTT
TTTAAGCCCAGTTGAATTAGTATATTTTAAACATGTATTTTTCAATAATAA
TTTTTCTTAGAGCTAAAACTTTCAGTTTTTTAGCTAACAATAAAAACATTCA
CGGAATTCTTTGCTGGGTTTTAAATTCATGGTTTATTTTTATCCTTTTTGAT
CCTGAAGCATGCCAGATTAACAAGTCTGAATCATTGAGTTTTTATTTATGTA
AATGTTATAATTACATTTTAATAACATGCGTAGGCAGTTATTTTATAACATT
ATTTTTCTAAAGTTGCATTATCGTAAATTATGTCTTTAGTCGTAGATATAAG
CACAATTTATTATGTAGGCAATGATTtAACTATTGTATAGTTCAATAATTTA
AAAGAGTAAAATTTTACACTATGAGTTCTAGAAAATACATGTTTATACGTAC
AGCCACAGTTTACCTTTTGCTAGTCCTAGTAAATGCTAATTATTCAATTCTC
TTACTCATCATCACATTTTCTATTCTCTCCATTTTGTACAATTTACATCACT
CCCACCTTCCCAAAGCATTATCTGGGCAGCTTTGAATGGAAAACAGTCATGA
ATGAGCAATCAATGGCTATTCACTACAAAATGGTGGAGAGGTGACTAAAAGT
TTATCTTAGACAAATTTTATATCATATATTTAGTTAGTTTCTTCCTATCACC
TgGCAATGCCAGCTCCTCCTCTGTTCtTTTTTTCCTATATAGTGCCTTCCCA
GTCATATCCTGTTCCTAAACCCGTTTAAGATGAATAGGTAATGGCCACATAT
CAAATACTAGTGTTATGAATTAGATCAACAAAATATGAAATAtTAAAATGTA
AGGATTGCCTATCTGTTGCAAATATAAGTTTTTTCTCTTGCAAAAATTATA
GGGGATGGAGTGTTAGATCTCTACAAAGAAAACCAGCATAAAATCTGAAG
AGTCATCCATATGTGATCCTTCTTCTGAAAATTCAGTGGCTGGGAGACTACA
CAGAAACAGAGAGGACTATGTGGAAGAAGTGCTGAGTTTGCAGATGGTTTG
CTCTCAAAAGCTTTGAAAGACATTCAGTCTGGAGCACTGGACATAAATAAAG
CAGGCATACTTTATGGCATACCTCAAAAACTTTACTTCTTCACTTAGAAGC
CTTACCAGCAGGGAAGCCTGCATCTTTTAAAAACAAAACTCGAGATTTCCAT
```

Figure 2 B cont.

```
GATAGTTATTCATATAAGGACAGTAAAGAAACTTGTGCAGTGCTGCAAAAAG
TAGCCTTGTGGGCAAGAGCTCAAGCAGAGCGCACAGAAAAAAGTAAACTCAA
TCTACTTGAAACCTCAGAAATAAAATTCCCAACAGCTTCCACTTACCTCCAT
CAGCTAACTCTACAGAAATGGTCACTCAGTTTAAAGAAAAAAATGAAAGCC
TCCAATATGAAACTTCAAATCCTACTGTACAGTTAAAAATTCCTCAGCTACG
AGTAAGTTCTGTCTCAAAATCACAACCTGATGGTTCTGGTCTGTTGGATGTT
ATGTATCAAGTTTCCAAAACCTCTTCAGTCCTAGAAGGATCAGCTCTCCAAA
AACTGAAAATATACTCCCTAAACAGAACAAAATAGAATGTTCTGGGCCTGT
AACTCACTCAAGTGTTGACTCTTACTTTCTACATGGGGACCTCTCTCCTTTG
TGTCTTAATTCTAAAAATGGAACAGTTGATGGAACCTCTGAAAATACTGAAG
ATGGATTAGATCGAAAAGACAGTAAGCAGCCCAGGAAAAAACGTGGCCGCTA
TCGGCAATATGATCATGAAATAATGGAAGAAGCTATTGCAATGGTAATGAGC
GGAAAAATGAGTGTTTCCAAAGCACAAGGAATTTATGGGGTACCTCACAGCA
CTTTAGAATACAAGGTAAAAGAAAGATCTGGAACACTGAAGACTCCTCCGAA
GAAGAAACTACGATTACCAGACACTGGGTTATATAATATGACAGATTCAGGG
ACTGGCAGCTGCAAAAACAGCAGCAAGCCTGTGTAGATTACTTGTTAGGAAA
ATGTTTGTGAGTGTGTGTGTGTGTGTGTGTGTTTGCGTGTGTGTGTATGTGC
ACAGGTGTGTATTTGTGTGTCTATATACACGTGGGAATTACAAATGCTCA
CTCTGACAGGAGACATGAAATTTTACAGTTCaAAAACCACTTACATGCCTTT
TGAAAAAAGTTTTATTCAGGGTTTTCACTGTGGACAGAATTATATAGTTGC
TTACTTAATTCTGATAGTTTGTATTTAATCCTTGTATAAATAGGTGAAAAAG
ATTCAGGTTTTCTTTAGTAGTCAATAGCATAAAGCGTTGTGGGAAAACGAGT
AATTGTCAAGTGAAACATTTTTATTGGTGAAAGACCATTCCAGCCATTCAGT
TGAACCATCTTATAATGGAAATATGATATTCATAGTTTATAAACATTCTATA
CAACAGACTTAACACTTGTTGTATGTATGTCAAGCAACCAATCAAAGTTTAA
ATAGCTATCTCCATACTAAGAAAAATTAATATATACAGTATTAGTACACGAC
AGTGCATTCTATGAAATACAAAATGCACTCAAGTGCATCCACCAGGAATAGA
AAAGAAACCTTAAAGGATATGTATAATGAAATTTAATATTTATCATTTAAT
AGTTGATTTAGCAAGAAGTTGGGGTTTATAAGGTATATACTTTAAAAAAACT
GACACATAGTTAACCCCAGCAGCTATAGAACCCTTTAATATAATAAGATGGA
GTACTAAGAACAAAAAATAATTTAAATTTAATTATTAAAATAATTTAGTTTT
GTTTTTCATTTGAAAAATAAGCTAATGTGTAAGGTTAGAAAAGAAAGTTGGA
ATGCAACTTAGAGCATGTTTATAATGTGCACAGAAAAGCTTGAGAATGATA
ATTTTGGTTTAAATGTGCTGGTTAGTTGATGTTATGACTACTTTAAATTTTA
AGGATTGTGACACACTCCTACTATTGAAAAACCTCAGTGTAACTTTAATATA
TTTGCTGCTGTGACATTTCAAAACATTTTCAGTTTATCAAAATGAATTGCAG
ATTTCATTTTGGTGGGCGATACATTATCATTTTGCTAATAACCAAATTTGCA
GTTTGTTCAGGGTCTTGAATAGATTTACAAATATTTAACACTGAAGCTGTTT
TGAACTTTCAGTAATGTAAACTCTCTACTAATTGGGTAGTTAGAAGCTGGGC
AGTGCATTTTAACTTTTACTAGACTCATAAGAGAGACTGGTCATTTTTACCT
AGCAGTTTTAAAATATGGGTCAAAGTATCCTTGTTGGATTTATGGAGTATGC
```

Figure 2 B cont.

```
AACTGTAGTGGTAAAATGTTATAAAGCATATGCCTTCATATAAAGAATAGGG
ATTTGCTTTATGTATTCAAAATTCTCTGAGTGCCCCCTTTCTCTGTTAAAAT
TCAGGTTCTGATCATTTTTCTAAGCCAGTTTTCCTAAGTCCaAAAGGAATAC
TTTTAGCTGAATTTAAAAAATAAGTGCACCTTGTCAAATGCTTGTGTTTTTA
CACTTGTGTTTGTGTGTATTTAATAATCATATATACGTGTAATACTAAAGAG
ATTTTCAGCTATTAAATTTTAAAACTGCTTACATGTTTAAAGAAACTGAAGA
GTGAGAAACTACACAACCAAGCAGTTATTTGGTCTCTGAGATCTATACTTAA
CCCTCTTCAGCTATTAATGTTACCTGCACACTAGGGTATGAATCCTCTTTTT
TTTTTTTTTCACCCCAAGAAAATATACATAATAGATTACAGAACAGCAGATG
TCAGGGTCATCTTTCTTTTTAAAGAATTAAGCCATATTTTGTGAGGGCCAGA
ACTTGCATTATTTAGTATATTTCCCCCTTCCCCCAATGGAAAGCAAAGTTAA
AGGTAAAGTACATATTTCAAAACAATTTTATTGACCTCTTTATACAGAATTT
TACTTGGAAAACTTTGGGGGCTTTGAATGCATTACATAATATTTATATTGtA
TTGAGCTTTTTTATTCCTCACACTATATTTACATTAATAAATTGATTGAGAA
GTTTATAGTAAAGGGAAACTTACAGAACACTTTTGTATCATTTAAAAGATGA
CCTGACCAAAAACTTTACAGGATTCATAAATCAGGGATCATTTTGCTATTGA
CTTCACAGTAATCAGTAGTTTTATAGGTAATATTATAGTTAATTTGCAGCAT
TTTAGTACTTGTATTATTTATTTTTGGTCAGAAATAGTAAATTAAAATATTT
TTTGATAGTTTATAGGTAATAATCAACCCATAACTTTTAAAAGAAACAAAAC
ATTTCTATTATTGAGTTAACATTTGATTATACAAACTAGGAAAGGCAGGGAA
ATTCCCCTTCTCCCCAGTGATTCTATTAAGATGACCTTTATGTTAAACTTTC
AAAGTACTTTATGAATTTAGTTACCAGTTACTATTTATTAATTGACAATTTT
CTGAAAAATCCCGTTTCAGCAGACTTAATGAAGGTGAAAGCAACCCTTATGT
GCTTTCTACTTATTTGAATGTTCCTCAAGTATTTTATATTAAAAAAAAAAAG
AAGGAAAAGAGAAAACAGTGCCTCTGTTTTTAGAAAACTACTGCTCAGTAAA
GTTGTTTAAACCATTTCTGGTAGCTAATGACAATTTTATATTAAATTGTATA
CTAACTTTAGTGAGACTGATTTTTTTAGTTGTTTACAGTACAAATACTTGTA
TTTGTTTTTTAATTGCAGTATTTCCAATGTCGCAGTAATTTAGTAAAACTCT
GTGGCTGCCTTGATTTTGACAGATTTTGTTAATATAAACTGATTGTTAGGCA
ATTAGTTATATTTATGCATAAATCAATTGCACTATAATTCATGAATTATTTA
TTACAATATTTTCTAATGAATTCATGTATCTGTCTTGTGTTGTAAATGTACT
GTAATTCTGTTCCTACTTTGTGTTGTTATATATCTAAATCTGATTGTATGAA
TTTTAATTGTTCAGTTAACGTGTTTCTAGGTTGTAATTTGTAGTAAAGCACT
TCAATGCTTTTGCACTTAAATTTACAACACTGTTGGTGTGTGATTGATTTAC
TCATTCAGTAAAAGAAAAAAAGAAAAGCAAAAGGAAAAAAAA
```

Figure 4.

MKKMIRQFAIEYISKSGKTQENRNGSIGPSIVCKSIQMN
QAENSLQEEQEGPLDLTVNRMQEQNTQQGDGVLDLSTKK
TSIKSEESSICDPSSENSVAGRLHRNREDYVERSAEFAD
GLLSKALKDIQSGALDINKAGILYGIPQKTLLLHLEALP
AGKPASFKNKTRDFHDSYSYKDSKETCAVLQKVALWARA
QAERTEKSKLNLLETSEIKFPTASTYLHQLTLQKMVTQF
KEKNESLQYETSNPTVQLKIPQLRVSSVSKSQPDGSGLL
DVMYQVSKTSSVLEGSALQKLKNILPKQNKIECSGPVTH
SSVDSYFLHGDLSPLCLNSKNGTVDGTSENTEDGLDRKD
<u>SKQPRKKRGRYRQYDHEIMEEAIAMVMSGKMSVSKAQGI</u>
<u>YGVPHSTLEYKVKER</u>SGTLKTPPKKKLRLPDTGLYNMTD
SGTGSCKNSSKPV

SEQUENCE LISTING

<160> NUMBER OF SEQ ID NOS: 12

<210> SEQ ID NO 1
<211> LENGTH: 53
<212> TYPE: PRT
<213> ORGANISM: Drosophila melanogaster
<220> FEATURE:
<221> NAME/KEY: MISC_FEATURE
<222> LOCATION: (1)..(54)
<223> OTHER INFORMATION: X can be any amino acid

<400> SEQUENCE: 1

Lys Gly Thr Arg Pro Lys Arg Gly Lys Tyr Arg Asn Tyr Asp Arg Asp
1               5                   10                  15

Ser Leu Val Glu Ala Val Lys Ala Val Gln Arg Gly Glu Met Ser Val
            20                  25                  30

His Arg Ala Gly Ser Tyr Tyr Gly Val Pro His Ser Thr Leu Glu Tyr
        35                  40                  45

Lys Val Lys Glu Arg
    50

<210> SEQ ID NO 2
<211> LENGTH: 53
<212> TYPE: PRT
<213> ORGANISM: Homo sapiens
<220> FEATURE:
<221> NAME/KEY: MISC_FEATURE
<222> LOCATION: (1)..(54)
<223> OTHER INFORMATION: X CAN BE ANY AMINO ACID

<400> SEQUENCE: 2

Lys Gln Pro Arg Lys Lys Arg Gly Arg Tyr Arg Gln Tyr Asp His Glu
1               5                   10                  15

Ile Met Glu Glu Ala Ile Ala Met Val Met Ser Gly Lys Met Ser Val
            20                  25                  30

Ser Lys Ala Gln Gly Ile Tyr Gly Val Pro His Ser Thr Leu Glu Tyr
        35                  40                  45

Lys Val Lys Glu Arg
    50

<210> SEQ ID NO 3
<211> LENGTH: 54
<212> TYPE: PRT
<213> ORGANISM: T. nigroviridis

<400> SEQUENCE: 3

Lys Gln Pro Arg Lys Lys Arg Gly Arg Tyr Arg Gln Tyr Asp His Asp
1               5                   10                  15

Leu Leu Glu Glu Ala Ser Ile Thr Met Val Met Ala Gly Arg Met Ser
            20                  25                  30

Val Ser Lys Ala Gln Gly Val Thr Gly Ile Pro His Ser Thr Leu Glu
        35                  40                  45

Tyr Lys Val Lys Glu Arg
    50

<210> SEQ ID NO 4
<211> LENGTH: 53
<212> TYPE: PRT
<213> ORGANISM: M. musculus
<220> FEATURE:
<221> NAME/KEY: MISC_FEATURE

```
<222> LOCATION: (1)..(54)
<223> OTHER INFORMATION: X can be any amino acid

<400> SEQUENCE: 4

Lys His Pro Arg Lys Lys Arg Gly Arg Tyr Arg Gln Tyr Asn Ser Glu
1               5                   10                  15

Ile Leu Glu Glu Pro Ile Ser Val Leu Met Ser Gly Lys Met Ser Val
                20                  25                  30

Ser Lys Ala Gln Ser Ile Tyr Gly Ile Pro His Ser Thr Leu Glu Tyr
            35                  40                  45

Lys Val Lys Glu Arg
    50

<210> SEQ ID NO 5
<211> LENGTH: 53
<212> TYPE: PRT
<213> ORGANISM: Caenorhabditis elegans
<220> FEATURE:
<221> NAME/KEY: MISC_FEATURE
<222> LOCATION: (1)..(54)
<223> OTHER INFORMATION: X CAN BE ANY AMINO ACID

<400> SEQUENCE: 5

Lys Arg Ser Arg Pro Lys Arg Gly Gln Tyr Arg Lys Tyr Asp Lys Asn
1               5                   10                  15

Ala Leu Asp Glu Ala Val Arg Ser Val Arg Arg Gly Glu Met Thr Val
                20                  25                  30

His Arg Ala Gly Ser Phe Phe Gly Val Pro His Ser Thr Leu Glu Tyr
            35                  40                  45

Lys Val Lys Glu Arg
    50

<210> SEQ ID NO 6
<211> LENGTH: 4958
<212> TYPE: DNA
<213> ORGANISM: Homo sapiens

<400> SEQUENCE: 6
cggagccctc ggtgcgcggc ggagagaaga ggattccggc gggaactcga ctcttggcgc      60
caccgcctca tgcactgtgt agctcagtac taaaacatca gtgggagaaa acaagggtt     120 ttgagagtat tttagaaggg ctttatggac cacggctacg aagagacctc agtttatttg    180
aagactgtga accagaagag ctgactgact ggtctatgga tgaaaaatgt tcattttgta    240
acctacagag agaagcagtc agtgattgta taccatctct tgattcttca cagtcaacac    300
caacagagga gctatcatct cagggccagt ccaacactga taagattgaa tgccaagcag    360
aaaattacct aaatgcactc tttcgaaaga agctgattca agcatctggg tctccaaga     420 ggtctcctac caatggttgg atcttcctca gaactgtgat cctaacattc ccctagttgc    480
tcaggaatta atgaaaaaga tgatacgtca atttgcgatt gagtacattt caaaaagtgg    540
taaaactcaa gagaatagaa atggttcaat tggaccaagt atagtatgta aaagtatcca    600
aatgaatcaa gcagaaaact cccttcagga agagcaggaa ggcccttag acctcactgt      660 gaatcgaatg caagaacaaa atactcagca agggatggg tgttagatc tctctacaaa     720 gaaaaccagc ataaaatctg aagagtcatc catatgtgat ccttcttctg aaaattcagt    780
ggctgggaga ctacacagaa acagagagga ctatgtggaa agaagtgctg agtttgcaga    840
tggtttgctc tcaaaagctt tgaaagacat tcagtctgga gcactggaca taaataaagc    900
```

```
aggcatactt tatggcatac ctcaaaaaac tttacttctt cacttagaag ccttaccagc      960
agggaagcct gcatctttta aaacaaaac tcgagatttc catgatagtt attcatataa     1020
ggacagtaaa gaaacttgtg cagtgctgca aaaagtagcc ttgtgggcaa gagctcaagc     1080
agagcgcaca gaaaaaagta aactcaatct acttgaaacc tcagaataa aattcccaac     1140 agcttccact tacctccatc agctaactct acagaaaatg gtcactcagt ttaaagaaaa     1200
aaatgaaagc ctccaatatg aaacttcaaa tcctactgta cagttaaaaa ttcctcagct     1260
acgagtaagt tctgtctcaa aatcacaacc tgatggttct ggtctgttgg atgttatgta     1320
tcaagtttcc aaacctctt cagtcctaga aggatcagct ctccaaaaac tgaaaaatat     1380
actccctaaa cagaacaaaa tagaatgttc tgggcctgta actcactcaa gtgttgactc     1440
ttactttcta catggggacc tctctccttt gtgtcttaat tctaaaaatg gaacagttga     1500
tggaacctct gaaaatactg aagatggatt agatcgaaaa gacagtaagc agcccaggaa     1560
aaaacgtggc cgctatcggc aatatgatca tgaaataatg gaagaagcta ttgcaatggt     1620
aatgagcgga aaaatgagtg tttccaaagc acaaggaatt tatggggtac ctcacagcac     1680
tttagaatac aaggtaaaag aaagatctgg aacactgaag actcctccga agaagaaact     1740
acgattacca gacactgggt tatataatat gacagattca gggactggca gctgcaaaaa     1800
cagcagcaag cctgtgtaga ttacttgtta ggaaaatgtt tgtgagtgtg tgtgtgtgtg     1860
tgtgtgtttg cgtgtgtgtg tatgtgcaca ggtgtgtatt tgtgtgtcta tatacacacg     1920
tgggaattac aaatgctcac tctgacagga gacatgaaat tttacagttc aaaaaccact     1980
tacatgcctt ttgaaaaaaa gttttattca gggttttcac tgtggacaga attatatagt     2040
tgcttactta attctgatag tttgtattta atccttgtat aaataggtga aaagattca     2100 ggttttcttt agtagtcaat agcataaagc gttgtgggaa aacgagtaat tgtcaagtga     2160
aacattttta ttggtgaaag accattccag ccattcagtt gaaccatctt ataatggaaa     2220
tatgatattc atagttttata aacattctat acaacagact taacacttgt tgtatgtatg     2280
tcaagcaacc aatcaaagtt taaatagcta tctccatact aagaaaaatt aatatataca     2340
gtattagtac acgacagtgc attctatgaa atacaaaatg cactcaagtg catccaccag     2400
gaatagaaaa gaaaacctta aaggatatgt ataatgaaat ttaatatta tcatttaata     2460 gttgatttag caagaagttg gggtttataa ggtatatact ttaaaaaaac tgacacatag     2520
ttaaccccag cagctataga acccttaat ataataagat ggagtactaa gaacaaaaaa     2580 taattaaat ttaattatta aaataattta gttttgtttt tcatttgaaa aataagctaa     2640
tgtgtaaggt tagaaaagaa agttggaatg caacttagag catgtttata atgtgcacag     2700
aaaaagcttg agaatgataa ttttggttta aatgtgctgg ttagttgatg ttatgactac     2760
tttaaatttt aaggattgtg acacactcct actattgaaa aacctcagtg taacttaat     2820 atatttgctg ctgtgacatt tcaaaacatt ttcagtttat caaaatgaat tgcagatttc     2880
attttggtgg gcgatacatt atcattttgc taataaccaa atttgcagtt tgttcagggt     2940
cttgaataga tttacaaata tttaacactg aagctgtttt gaactttcag taatgtaaac     3000
tctctactaa ttgggtagtt agaagctggg cagtgcattt taactttac tagactcata     3060 agagagactg gtcattttta cctagcagtt ttaaatatg ggtcaaagta tccttgttgg     3120
atttatggag tatgcaactg tagtggtaaa atgttataaa gcatatgcct tcatataaag     3180
aatagggatt tgctttatgt attccaaaat tctctgagtg ccccctttct cctgttaaaa     3240
ttcaggttct gatcattttt tctaagccag ttttcctaag gtccaaaagg aatacttta     3300
```

-continued

```
gctgaattta aaaataagt gcaccttgtc aaatgcttgt gttttacac ttgtgtttgt    3360 gtgtatttaa taatcatata tacgtgtaat actaaagaga ttttcagcta ttaaatttta    3420
aaactgctta catgttaaa gaaactgaag agtgagaaac tacacaacca agcagttatt    3480
tggtctctga gatctatact taaccctctt cagctattaa tgttacctgc acactagggt    3540
atgaatcctc ttttttttt ttttcacccc aagaaaatat acataataga ttacagaaca    3600
gcagatgtca gggtcatctt tctttttaaa gaattaagcc atattttgtg agggccagaa    3660
cttgcattat ttagtatatt tcccccttcc cccaatggaa agcaaagtta aggtaaagt     3720 acatatttca aaacaatttt attgacctct ttatacagaa ttttacttgg aaaactttgg    3780
gggctttgaa tgcattacat aatatttata ttgtattgag ctttttatt cctcacacta    3840 tatttacatt aataaattga ttgagaagtt tatagtaaag ggaaacttac agaacacttt    3900
tgtatcattt aaaagatgac ctgaccaaaa actttacagg attcataaat cagggatcat    3960
tttgctattg acttcacagt aatcagtagt tttataggta atattatagt taatttgcag    4020
cattttagta cttgtattat ttatttttgg tcagaaatag taaattaaaa tatttttga    4080 tagtttatag gtaataatca acccataact tttaaaagaa acaaaacatt tctattattg    4140
agttaacatt tgattataca aactaggaaa ggcagggaaa ttcccttct ccccagtgat    4200 tctattaaga tgacctttat gttaaacttt caaagtactt tatgaattta gttaccagtt    4260
actatttatt aattgacaat tttctgaaaa atcccgttc agcagactta atgaaggtga    4320
aagcaaccct tatgtgcttt ctacttattt gaatgttcct caagtatttt atattaaaaa    4380 aaaaagaag gaaagagaa aacagtgcct ctgttttag aaaactactg ctcagtaaag    4440
ttgtttaaac catttctggt agctaatgac aatttatat taaattgtat actaacttta    4500
gtgagactga tttttttagt tgtttacagt acaaatactt gtatttgttt tttaattgca    4560
gtatttccaa tgtcgcagta atttagtaaa actctgtggc tgccttgatt ttgacagatt    4620
ttgttaatat aaactgattg ttaggcaatt agttatattt atgcataaat caattgcact    4680
ataattcatg aattatttat tacaatattt tctaatgaat tcatgtatct gtcttgtgtt    4740
gtaaatgtac tgtaattctg ttcctacttt gtgttgttat atatctaaat ctgattgtat    4800
gaattttaat tgttcagtta acgtgtttct aggttgtaat ttgtagtaaa gcacttcaat    4860
gcttttgcac ttaaatttac aacactgttg gtgtgtgatt gatttactca ttcagtaaaa    4920 gaaaaaaga aaagcaaaag gaaaaaaaaa aaaaaaa                              4958
```

<210> SEQ ID NO 7
<211> LENGTH: 6074
<212> TYPE: DNA
<213> ORGANISM: Homo sapiens

<400> SEQUENCE: 7

```
ctacattgtg ttctgagtgg ggctgatgag ttagatttgg tgagaattag gaggggttgc     60
cggggtgagg cggggggtcag gaggagaaga gtatgaatct tctaggcaga ggaaaccaat    120
tccaagtgtg aaagcccaga acgagaaat agcatagcac tttcccagca ggtttccctg     180
ctccaccttt agctccttgc ggtccattct cccatagcag attgatcttt taaaaaccta    240
aattgaaatc atgtcagtct tccacccaga attctccagt ggcttcctgt ctctgtcaga    300
atgaaatgcg aagttcttgc catggcccaa tggccctgtt taacctcttc ctataacatt    360
tctgatctca gctcactctt ggcctggctt ccttcatttt agatacctg gcctttgcta    420
```

-continued

```
ttcctctgac attccagaca tggttccata tcacagcccc tatacagact gttctttt gg      480 aaacgttctc ccatgtatct gattagttgg tgatcctcac cttattcagg gccctgttca       540
aatcaaagaa gcctgcactg ataacactgt gtaaaacagc agcattctca gccccaccct       600
cattactcta tcagcttact ctgtgttatt ttccagggtg gcactatcat aattgctggt       660
ggtagtggtg ctggttgtgg tgttgtatga attatctcat tagatcctaa gcactatgac       720
tatgacaata ggtactttgt atgactttt tttttgatgc tcttctagtg cctaaaatag        780
tgctttgcat atagtgagcg ctcaataaat tattgtcgaa gtctatatag gaggctatag       840
ataggatgtt ttgttttatt tttcatcttt gtatctgccc aggaacatac atatttcatg      900
gattgattat ggttacagta aaacccagtt gaattttta agcccagttg aattagtata       960
tttttaaaca tgtattttc aataataatt tttcttagag ctaaaacttt cagtttttta       1020
gctaacaata aaacattca cggaattctt tgctgggttt taaattcatg gtttattttt       1080 atccttttg atcctgaagc atgccagatt aacaagtctg aatcattgag ttttattta         1140 tgtaaatgtt ataattacat tttaataaca tgcgtaggca gttatttat aacattattt        1200 ttctaaagtt gcattatcgt aaattatgtc tttagtcgta gatataagca caatttatta      1260
tgtaggcaat gatttaacta ttgtatagtt caataattta aaagagtaaa attttacact      1320
atgagttcta gaaatacat gtttatacgt acagccacag tttacctttt gctagtccta       1380
gtaaatgcta attattcaat tctcttactc atcatcacat tttctattct ctccattttg      1440
tacaatttac atcactccca ccttcccaaa gcattatctg ggcagctttg aatggaaaac      1500
agtcatgaat gagcaatcaa tggctattca ctacaaaatg gtggagaggt gactaaaagt     1560
ttatcttaga caaattttat atcatatatt tagttagttt cttcctatca cctggcaatg     1620
ccagctcctc ctctgttctt ttttt cctat atagtgcctt cccagtcata tcctgttcct    1680
aaacccgttt aagatgaata ggtaatggcc acatatcaaa tactagtgtt atgaattaga     1740
tcaacaaaat atgaaatatt aaaatgtaag gattgcctat ctgttgcaaa tataaagttt     1800
tttctcttgc aaaaattata ggggatggag tgttagatct ctctacaaag aaaaccagca     1860
taaaatctga agagtcatcc atatgtgatc cttcttctga aaattcagtg gctgggagac     1920
tacacagaaa cagagaggac tatgtggaaa gaagtgctga gtttgcagat ggtttgctct     1980
caaaagcttt gaaagacatt cagtctggag cactggacat aaataaagca ggcatacttt    2040
atggcatacc tcaaaaaact ttacttcttc acttagaagc cttaccagca gggaagcctg     2100
catcttttaa aaacaaaact cgagatttcc atgatagtta ttcatataag gacagtaaag     2160
aaacttgtgc agtgctgcaa aaagtagcct tgtgggcaag agctcaagca gagcgcacag    2220
aaaaaagtaa actcaatcta cttgaaacct cagaaataaa attcccaaca gcttccactt     2280
acctccatca gctaactcta cagaaaatgg tcactcagtt taaagaaaaa aatgaaagcc    2340 tccaaatga aacttcaaat cctactgtac agttaaaaat tcctcagcta cgagtaagtt    2400
ctgtctcaaa atcacaacct gatggttctg gtctgttgga tgttatgtat caagtttcca    2460
aaacctcttc agtcctagaa ggatcagctc tccaaaaact gaaaaatata ctccctaaac    2520
agaacaaaat agaatgttct gggcctgtaa ctcactcaag tgttgactct actttctac     2580 atggggaccct ctctccttt g tgtcttaatt ctaaaaatgg aacagttgat ggaacctctg   2640
aaaatactga agatggatta gatcgaaaag acagtaagca gcccaggaaa aaacgtggcc    2700
gctatcggca atatgatcat gaaataatgg aagaagctat tgcaatggta atgagcggaa    2760
aaatgagtgt ttccaaagca caaggaattt atggggtacc tcacagcact ttagaataca    2820
```

-continued

```
aggtaaaaga aagatctgga acactgaaga ctcctccgaa gaagaaacta cgattaccag   2880
acactgggtt atataatatg acagattcag ggactggcag ctgcaaaaac agcagcaagc   2940
ctgtgtagat tacttgttag gaaaatgttt gtgagtgtgt gtgtgtgtgt gtgtgtttgc   3000
gtgtgtgtgt atgtgcacag gtgtgtattt gtgtgtctat atacacacgt gggaattaca   3060
aatgctcact ctgacaggag acatgaaatt ttacagttca aaaaccactt acatgccttt   3120
tgaaaaaaag ttttattcag ggttttcact gtggacagaa ttatatagtt gcttacttaa   3180
ttctgatagt ttgtatttaa tccttgtata aataggtgaa aaagattcag gttttcttta   3240
gtagtcaata gcataaagcg ttgtgggaaa acgagtaatt gtcaagtgaa acattttat   3300 tggtgaaaga ccattccagc cattcagttg aaccatctta taatgaaat atgatattca   3360 tagtttataa acattctata caacagactt aacacttgtt gtatgtatgt caagcaacca   3420
atcaaagttt aaatagctat ctccatacta agaaaaatta atatatacag tattagtaca   3480
cgacagtgca ttctatgaaa tacaaaatgc actcaagtgc atccaccagg aatagaaaag   3540
aaaaccttaa aggatatgta taatgaaatt taatatttat catttaatag ttgatttagc   3600
aagaagttgg ggtttataag gtatatactt taaaaaaact gacacatagt taaccccagc   3660
agctatagaa cccttaata taataagatg gagtactaag aacaaaaaat aatttaaatt   3720
taattattaa aataatttag ttttgttttt catttgaaaa ataagctaat gtgtaaggtt   3780
agaaaagaaa gttggaatgc aacttagagc atgtttataa tgtgcacaga aaaagcttga   3840
gaatgataat tttggtttaa atgtgctggt tagttgatgt tatgactact ttaaattta   3900 aggattgtga cacactccta ctattgaaaa acctcagtgt aactttaata tatttgctgc   3960
tgtgacattt caaaacattt tcagtttatc aaaatgaatt gcagatttca ttttggtggg   4020
cgatacatta tcattttgct aataaccaaa tttgcagttt gttcagggtc ttgaatagat   4080
ttacaaatat ttaacactga agctgttttg aactttcagt aatgtaaact ctctactaat   4140
tgggtagtta gaagctgggc agtgcatttt aacttttact agactcataa gagagactgg   4200 tcattttac ctagcagttt taaaatatgg gtcaaagtat ccttgttgga tttatggagt   4260
atgcaactgt agtggtaaaa tgttataaag catatgcctt catataaaga atagggattt   4320
gctttatgta ttcaaaattc tctgagtgcc cccttctct gttaaaattc aggttctgat   4380 cattttcta agccagtttt cctaagtcca aaaggaatac ttttagctga atttaaaaaa   4440
taagtgcacc ttgtcaaatg cttgtgtttt tacacttgtg tttgtgtgta tttaataatc   4500
atatatacgt gtaatactaa agagattttc agctattaaa ttttaaaact gcttacatgt   4560
ttaaagaaac tgaagagtga gaaactacac aaccaagcag ttatttggtc tctgagatct   4620
atacttaacc ctcttcagct attaatgtta cctgcacact agggtatgaa tcctctttt   4680 tttttttttc accccaagaa aatatacata atagattaca gaacagcaga tgtcagggtc   4740
atctttcttt ttaaagaatt aagccatatt ttgtgagggc cagaacttgc attatttagt   4800
atatttcccc cttccccaa tggaaagcaa agttaaaggt aaagtacata tttcaaaaca   4860
attttattga cctcttata cagaatttta cttggaaaac tttggggct ttgaatgcat   4920 tacataaatat ttatattgta ttgagctttt ttattcctca cactatattt acattaataa   4980
attgattgag aagtttatag taaagggaaa cttacagaac acttttgtat catttaaaag   5040
atgacctgac caaaaacttt acaggattca taaatcaggg atcatttgc tattgacttc   5100 acagtaatca gtagttttat aggtaatatt atagttaatt tgcagcattt tagtacttgt   5160
```

-continued

```
attatttatt tttggtcaga aatagtaaat taaaatatttt tttgatagtt tataggtaat     5220
aatcaaccca taacttttaa aagaaacaaa acatttctat tattgagtta acatttgatt     5280
atacaaacta ggaaaggcag ggaaattccc cttctcccca gtgattctat taagatgacc     5340
tttatgttaa actttcaaag tactttatga atttagttac cagttactat ttattaattg     5400
acaattttct gaaaaatccc gtttcagcag acttaatgaa ggtgaaagca acccttatgt     5460
gctttctact tatttgaatg ttcctcaagt attttatatt aaaaaaaaaa agaaggaaaa     5520
gagaaaacag tgcctctgtt tttagaaaac tactgctcag taaagttgtt taaaccatt t     5580
ctggtagcta atgacaattt tatattaaat tgtatactaa ctttagtgag actgattttt     5640
ttagttgttt acagtacaaa tacttgtatt tgttttttaa ttgcagtatt tccaatgtcg     5700
cagtaattta gtaaaactct gtggctgcct tgattttgac agattttgtt aatataaact     5760
gattgttagg caattagtta tatttatgca taaatcaatt gcactataat tcatgaatta     5820
tttattacaa tattttctaa tgaattcatg tatctgtctt gtgttgtaaa tgtactgtaa     5880
ttctgttcct actttgtgtt gttatatatc taaatctgat tgtatgaatt ttaattgttc     5940
agttaacgtg tttctaggtt gtaatttgta gtaaagcact tcaatgcttt tgcacttaaa     6000
tttacaacac tgttggtgtg tgattgattt actcattcag taaaagaaaa aagaaaagc      6060
aaaaggaaaa aaaa                                                       6074
```

<210> SEQ ID NO 8
<211> LENGTH: 442
<212> TYPE: PRT
<213> ORGANISM: Homo sapiens

<400> SEQUENCE: 8

```
Met Lys Lys Met Ile Arg Gln Phe Ala Ile Glu Tyr Ile Ser Lys Ser
1               5                   10                  15

Gly Lys Thr Gln Glu Asn Arg Asn Gly Ser Ile Gly Pro Ser Ile Val
            20                  25                  30

Cys Lys Ser Ile Gln Met Asn Gln Ala Glu Asn Ser Leu Gln Glu Glu
        35                  40                  45

Gln Glu Gly Pro Leu Asp Leu Thr Val Asn Arg Met Gln Glu Gln Asn
    50                  55                  60

Thr Gln Gln Gly Asp Gly Val Leu Asp Leu Ser Thr Lys Lys Thr Ser
65                  70                  75                  80

Ile Lys Ser Glu Glu Ser Ser Ile Cys Asp Pro Ser Ser Glu Asn Ser
                85                  90                  95

Val Ala Gly Arg Leu His Arg Asn Arg Glu Asp Tyr Val Glu Arg Ser
            100                 105                 110

Ala Glu Phe Ala Asp Gly Leu Leu Ser Lys Ala Leu Lys Asp Ile Gln
        115                 120                 125

Ser Gly Ala Leu Asp Ile Asn Lys Ala Gly Ile Leu Tyr Gly Ile Pro
    130                 135                 140

Gln Lys Thr Leu Leu Leu His Leu Glu Ala Leu Pro Ala Gly Lys Pro
145                 150                 155                 160

Ala Ser Phe Lys Asn Lys Thr Arg Asp Phe His Asp Ser Tyr Ser Tyr
                165                 170                 175

Lys Asp Ser Lys Glu Thr Cys Ala Val Leu Gln Lys Val Ala Leu Trp
            180                 185                 190

Ala Arg Ala Gln Ala Glu Arg Thr Glu Lys Ser Lys Leu Asn Leu Leu
        195                 200                 205
```

```
Glu Thr Ser Glu Ile Lys Phe Pro Thr Ala Ser Thr Tyr Leu His Gln
    210                 215                 220

Leu Thr Leu Gln Lys Met Val Thr Gln Phe Lys Glu Lys Asn Glu Ser
225                 230                 235                 240

Leu Gln Tyr Glu Thr Ser Asn Pro Thr Val Gln Leu Lys Ile Pro Gln
                245                 250                 255

Leu Arg Val Ser Ser Val Ser Lys Ser Gln Pro Asp Gly Ser Gly Leu
            260                 265                 270

Leu Asp Val Met Tyr Gln Val Ser Lys Thr Ser Val Leu Glu Gly
        275                 280                 285

Ser Ala Leu Gln Lys Leu Lys Asn Ile Leu Pro Lys Gln Asn Lys Ile
    290                 295                 300

Glu Cys Ser Gly Pro Val Thr His Ser Ser Val Asp Ser Tyr Phe Leu
305                 310                 315                 320

His Gly Asp Leu Ser Pro Leu Cys Leu Asn Ser Lys Asn Gly Thr Val
                325                 330                 335

Asp Gly Thr Ser Glu Asn Thr Glu Asp Gly Leu Asp Arg Lys Asp Ser
            340                 345                 350

Lys Gln Pro Arg Lys Lys Arg Gly Arg Tyr Arg Gln Tyr Asp His Glu
        355                 360                 365

Ile Met Glu Glu Ala Ile Ala Met Val Met Ser Gly Lys Met Ser Val
370                 375                 380

Ser Lys Ala Gln Gly Ile Tyr Gly Val Pro His Ser Thr Leu Glu Tyr
385                 390                 395                 400

Lys Val Lys Glu Arg Ser Gly Thr Leu Lys Thr Pro Pro Lys Lys Lys
                405                 410                 415

Leu Arg Leu Pro Asp Thr Gly Leu Tyr Asn Met Thr Asp Ser Gly Thr
            420                 425                 430

Gly Ser Cys Lys Asn Ser Ser Lys Pro Val
        435                 440

<210> SEQ ID NO 9
<211> LENGTH: 9574
<212> TYPE: DNA
<213> ORGANISM: Drosophila melanogaster

<400> SEQUENCE: 9
gttgctgtcg ataatttact ctgtgctcca catatatata tatatatata tatatatata      60
ttataaataa aaaccaacca atagcccaaa aaaaaaaaag aaatgaaaaa tccgcatcaa     120
caataaaaat ctgcctgcat ttttgccttt tgtgtgagct gcccagcaga acgagagaag     180 cactttttatt gtatataaaa attatatcaa tcgccaggag gagctgcagc aacccactcc     240
aagccaggtt gccacgtcct gagctgctgt aagttctccg cagcagctgc agcagcatca     300
gcatcgcagc agcatcagca gcagcgcaca atccgccgca gcatcaattt ggcttttggg     360
cagagataat ttaagacaaa tatatgtgat gctatgcaca tcagcagcta tgaaatatcc     420
ctagaacgcg ttgctgaaga atgtatgggt cgcaggcaat ggaaacatta tcaagacaaa     480
ctgacgtgca gccacttgaa tatcgaggag caacagccca tagcaatagc cggttccgag     540
gacgagccat cgcaatacaa ccacagcagc aaggagatca gccagagcaa tcccaaccac     600
tgtaagacag agaaccaccg tctggagcag caacacaacg gcagccagct attggaagaa     660
gaagattctg agaacaacca acatcacac gattcatcac gtacaccaac accgggagcc     720
accagtacac catcaccacc gccagaaccc atcgattgga gaccgtcggc caagtgcaac     780
```

```
ttctgtgtta acggtcgcct gctaacggtt aacgcccagg gcaagttggt ggccgagtca      840
gcagcaactg ccactagtag tagcactagt aatagtcaca ttcatcagca cgacagtgac      900
agcaactcga gtgcatcact gccccaccac atcagcagca gcagcagcag caacaacaat      960
agcagtggca acagggcacg ccacattgct gctgcaagtg caagagcaac accagcagcg     1020 gcccacacccg ccaactccct tgaactctac aagctgctga cccagcgggc agccaaaatg     1080
acatcgatgg actcgatggc cgcccagctg gcgcaattct cactgctggc cgacttcaat     1140
ctgatcaact cgctggccag ccaacagcag cagcagcagc agcaacagat cgctagtgcg     1200
gtaacgccaa ctacctcaga agtatctgca gccgcaatca gtcccgcact caaagataca     1260
cccagtccca gtgtggatgc accgctcgat cttagcagca aaccatcgcc gaactcatcg     1320
attagcggcg atgtgaagtc cgtcagagcc tgtgccacgc ccacgccgtc gggaagaagg     1380
gcgtacagtg aagaggatct gagccgggcc ctacaggatg tggtggccaa caagctagat     1440 gccccggaaat cggctagcca gcaccatgag cagcgctcca ttctggacaa ccggctgttc     1500
aagatgaaac accatgacca ggagcaggat catgatggcg acgagctcga ggactccaac     1560
gatgatgctg aggcggaagt ggacagcaat gcgtcgacac cggtgtatcc ggcagagttt     1620
gcaagggcac aactgcgcaa actgagccac ctgtccgagc acaatggcag cgatctgggc     1680
gaggatgtgg atcgtggatc gccgaaaatg gggcgacatc cggcctgtgg caatgccagt     1740
gccaatcagg gcgcaccggc atccattccg ctggatgcca atgtcctgct gcacactctg     1800
atgctggctc tgggattgg tgcaatgccg aagctggatg aaacgcaaac ggtgggcgac     1860
tttatcaagg gtctgctggt ggccaacagt ggtggcataa tgaacgaggg actgctaaat     1920
ctgctgtccg ccagtcagga gaacagcaat ggcaatgcct cgctgctgct gcaacagcaa     1980
cagcatcagc aacaccatca gcaacaccat cagcagcagc agcagcagca acatgtcgcc     2040
gcctaccggc atcgcctgcc caagtcgagag actccggaaa cgaactcctc gttggatccg     2100
aacgatgcca gcgaggatcc catactgaag attccgtcct tcaaggtcag cggtccggcc     2160
agcagcagca gcctgtcgcc gggcggactg gttggtggtc accaccatcc gctgaacaac     2220
aacaacagcc tcagcatcag caacaacagc aaccacagca gcaacagcca tcggaacggc     2280
agcaatcgca gcccgcattc cgcatcgccc atgctggccg cggccgtggc ccaaggtggc     2340
tactccgccg gcaacagttt gctgacctca tcctcgtcta gcatacagaa gatgatggcc     2400
agcaatatcc agcgccagat caacgaacag agtggccagg agagtctcag gaacggaaat     2460
gttagcgatt gcagcagcaa caatggcggc tcctcctcgc tgggatacaa gaagccgagc     2520
atttcggtgg ccaagatcat tggcggaacg gacacctcac ggttcggagc ctcgcccaat     2580
ctgctgtccc aacagcacca ttcggctcac cacctgaccc accagcaaca gcagcaacag     2640
ctgagcgccc aggaggcatt gggcaaggga acgcgaccaa agaggggcaa gtatcgcaac     2700
tatgaccgcg acagtttggt ggaggcggtc aaggcggtgc agagaggtga aatgtcggtt     2760
catcgagcgg gtagctacta cggcgtaccg cattccacac tggagtacaa ggtcaaggaa     2820
cgtcacctga tgcgaccgcg caagcgagag cccaagccgc agcccgatct cgtcggcctg     2880
accggaccag ccaacaagct gcagctggac aaactgaagg cgggaccaca tggtggctcc     2940
aagctgagca atgccctcaa gaaccaaaac aatcaggcgg ctgcggcggc ggcggcggca     3000
gcagcagcag cggccgctgc cacgcccaac ggcctgaaac tgccccttttt cgaggcgggt     3060 ccacaggcgt tatcctttca gccgaacatg ttctggcccc agacgaacgc cacgaatgcc     3120
tacggcctgg acttcaatcg catcacggag gcgatgcgga atccccaggc ctccaatcac     3180
```

-continued

```
cacggcctga tgaagagtgc ccaggacatg gtggagaacg tgtacgatgg catcatcagg    3240
aagacgctgc aggcgagcga gggcaatggc agtgcggcgg gtaatggcag caacggtagc    3300
aatggcaacg ggcatgggca cgggcatggc catggcacg ccctgctcga tcagctgctg     3360
gtgaagaaga ccccctgcc gttcaccaac catcggaaca atgactacgc cgccacctgt     3420
tcgagtgcca gcggggagag cgtaaagcgg tcggcagtc ccatgggcaa ctatgcagac     3480
atcaagcggg agcgcctgag cgccgacagc ggcggcagca gcgatgagga gcactcggcc    3540
agccacatca acaacaacaa cagcgatttg gcgcacaaca agaacaagag cggcggcggc    3600
ggcggcggcg gcggcaatgg ccagaccaat gggaacggca ggagcagccg gatgacgtcg    3660
cgggatgatt ccgaaacgga tgccagcagc tttaagagcg gcgaaaatgg cggccagcaa    3720
aaccacaaaa tgatggatct caatggcggc agcagcagca gcagtcacat caagtgcgaa    3780
tcggaggcgg ccaccggaca tcacagtcct ggacaccaca ccacgtccat actgcacgag    3840
aagctggccc agatcaaggc cgagcaagtg gaccaggcgg atcagttata ggagcagccg    3900
atggccgcga atccagcgtt cgcctggcca ccgctggccg cccactacta cagcttctag    3960
gcggagggag ggggaacacc aaattaagcc acgttttttg atagtaccat acaaatcact    4020
aaatagaatt atatatatat atatatatat atatattctt ttataatatt ttatgccagc    4080
cagctgaccg atgtgcgtgg taaatgtgcg ctagtcttag ttaaatgtgt aatcaactgc    4140
ataggggaaa aacaaaacca caggaaatca taaataacaa caaacaaaca aacaaacaaa    4200
aataacaaaa ataacaagaa ccgcaagcaa agaaacatac atttgtgccc cggagtgtac    4260
gatgtatatt tttgtttcgt tttgacaatc gacaaatagg cattctcttg tacaaacttt    4320
cttaaaagct aacaacaaaa caaatctaaa accttaagac caaaaaaaac aaaaaatgaa    4380
aaaaaacgaa tactgagcaa aaaccaagaa ccattttcat tttgcatttc gtttcgaacc    4440 gcattttgt gttgagcata ttttttactg aacagtaaat gaaacagtcc aatgggaaaa     4500
tatatgtata gcagaaatat atagcactta caagccaaca acttaatcga cttctgtttt    4560
ggtcaggttt ctggaccttg agctgcgatt ttcgcacatt ccataagata ctcttatgtt    4620
ccatataatt gtagttttca tacgcaaatt tctagagcag ttagagccgc agctcagaca    4680
gggccaaaac caaaaaaaat gaccaggcag ttgtcctcga catagacaca atgagtatag    4740
gccaacaaca gcaactacaa cagcaacaat aactacagca aagagaccat aacaacaaca    4800
acaacaacaa caacaacagt aacaaccata acaagcaaca acaacagcaa tatccgatca    4860
ataacaacaa ccaacaaaac aagcaataat aatacaagac tctacaatac aaagaaatga    4920
aacattgaaa tagcaaaatt caaaattcaa aaatataaac cgaaaaacca caatcaaaaa    4980
accaaaacaa aattatccac aaaaattcaa ccatttttta tgatttccaa aaggaggaaa    5040
atacaaaacg gaaatccaat taaccaaagc tgccttcaca tttaccaatt aaataaatta    5100
gtaagcaaag cgagacaaag cacacaaaat aataattcaa atgaaacgca aacgcagagt    5160
aaaaagcaag aaaatcaaac aatttccgaa atatcagtcc caaattacat ttttattttg    5220
aaaaattcca aaacctaaga atacaaaata ttacacccca aaacattcaa aattattttc    5280
attcggaaaa aaatttcaca catattcaaa taaagtaatc aaaattaaag tgtttcggtg    5340
ttaaaaaaaa ataaaaggga aaattaccga aatatatata tctgtgttta gactttaaaa    5400
cggaaatttg aaaacaaaat ttcaagattt cggcttaaaa gtaaaagag agacaaaaaa     5460 aaaacaaaac aaatgtttga gaacacacat ttcatgtaca gtcgcctaac caccaaaagt    5520
```

```
aagaaagcat aaatatataa agactttata ttactatata ccatatgata tatatttgta    5580
tatttatgta tgtgtgtgtc ttcatcacta cgcgtatacc ctcaaaccaa acacatgatc    5640
attttgagca actaaatata tttaaatgta cttatacact ctacacactc ttttacagga    5700
gagcaaaaca tatttacaca gttaaacccc ccccaatcca aatctttggc cctcctttcg    5760
acgtatctac atttcgtttg actttgaaat tctatctatg ggtaaacaac tactaactaa    5820
atgtctgcgt aaatgaaaat agatggccaa ttatataaat gtccctaaaa acacatattt    5880
tgtgtgctag ctagtaagtg tcaaaggaaa aacaaaaaaa ccatacaaaa acgatataca    5940
atatatttaa atgattatga gatggtgaaa attgtcggaa atatttgaaa atatttagcg    6000
aattataata caagaaacag tcaaaggtat ggcaaggaaa attgtggaaa atagcaagcg    6060
aaatgcgttt aataattata ttgaaatcat ttaaaggcat ttaatatatt tatcatttcc    6120
acgatgcgat tgataaaaca gtatttattg gctaatctcc ccaattacat ttgatgtgca    6180
taaatgttgt ggtttagaat caaaatcaaa ggtacaaaat taaaagttaa ggcttaaaaa    6240
tgtaaaaaaa aaatttaata caattatgaa ttttggtata atagcggaga gttctgcgaa    6300
cctaaagaaa ttcaaaatgt ttattatatg aaaatggaa aaatgaagg aaaaataggc    6360 gagagtagat aaagaatgga tggaaataaa tcaaaagta tttattgcta atttaattat    6420
atttgaagta tacatacata tttattatat acatacatat atattagaca ccctgtctgt    6480
gattaataat ccaaaatttt gaagagcatt ttctgaaata acgttggcta agcatatgcg    6540
aaaagacaaa accaatggat aaagtaacac acacccatgt aaagaaattg tagacagatc    6600
ggataaaacg aaactaaacc aagcacaagc taatggccca aatgcagttg gccccgaaaa    6660
tcgagcgctg catttggcca agagaatttc ttaagctacg gcacacatca ctgaaaacaa    6720
aaactgaaaa ctgaatactg aatactgcga ataggaaaca gtaagcagaa gacaagatcg    6780
atggtactgt tcagaacata tatagttgta tatattttgg aataatgttt accagttcaa    6840
gtcaaaatta aaaggaaaaa aaatgcaaag tcttttataa tgcaaaatta tacaaagaaa    6900
aattacaatt tcgcaacgct aaaaaatgaa aaacgaaaat attgatgtaa aaagaatgaa    6960
aatcaaactt aaaataataa acaagataaa gtgcaattat acggtttaaa taagcaaatt    7020
taagaaacaa acgttataaa caaaaacaca aacatgttaa aacaatgaaa atatttcgaa    7080
gcaagtttag ctacaaattc caaggcaact gataatgaca agaaccattt acaagaaaaa    7140
ccaagacagc aaagtacagt gcgtttcatg actcgcaaat acgggcaata gaatactagt    7200
ttttcattgc ccatggagaa ctgaaacgca ctttggccct cacttcatat tgatagggta    7260
atcggatcca aaatctgtaa accaaatttt gggatcagcg attaaaacct taacggaagt    7320
tcataactgc agaaaaaaaa agtcgaaagt cgaaatgtca acctagtggt agttcgaaac    7380
acaaaaacaa aacaaaccaa tcgagtgtaa ttgagtgaca gcttgagaat gttgaattgt    7440
atagaatttt tgcttgtgca cctggtcgag ggggccgtgg ttgcgccccc ttttggtttt    7500
ctaggtgaac aggcgaaaac gctcaggtac gtgttttatt tttcggagag aaacaagatt    7560
gattacccat acattactta ttctttgttt tactacaaca taatagttaa tatttgtata    7620
aaaaaaaaag acgacgatgg cgagaaggga aaaccagcta aaaaaattga tatattcata    7680
atatagaatt gttttaaatg gtttgagagc gaaaatatt gagggtttct agcgtgcttc    7740
atgaaattgc tcatatttgt gtataaaacc ttatttgttc aatgcgaatc aaaatttgct    7800
gaatataagt gcatatatat ataattagag tttatttttc ggtttagtta agcgcataca    7860
atgattacga tttaaataat tattattagt tatgacctaa tagtaggcaa atcaaaattt    7920
```

```
cttcacataa acaatcaac ttctactttc aaataatttc tagacgtatg taactatagg   7980
ttattattct attattatac ggcctaaaac tatttagcgc gttgttagac tcgatttatg   8040
gtttgtacat attagacaac attttatgg tattctcctc ttttttatt attactagca   8100
ttattactcc ctatttaat tgacttctta aatgggcaac atcattttga actatagtgc   8160
aattgtttca acaaaacca agcaaccaac aacaaatata ttaacattaa agattaatat   8220
aatttacaag ctttctttgc cgatgccaag aaggatgaat aacgcatatg tctaccgtat   8280
ggatcgaaaa tcaaaaatca ttttaagtgc acataactct ttaaaatagc aattagacta   8340
cgactaggtt tttccattat tatgcgcacg cttcagtcca aaaaaaaaa aattgaaatt   8400
cttcacattc tcattcacat gctcagttcg agacatcaca atcacaagcc agaaaaagaa   8460
aactcaaaac ttttcaccta agttcaactt gagcgaccgc aacaactcaa gatcagcaaa   8520
gatcacaagc gaaaattgct aagaaacaat agcccagacg tgataacaac acaaaaatag   8580
ccacaacaat agcccaaaaa taattgaaac aaaaattgat taaaagccaa aaaaaaaata   8640
aaaaagcaaa taataagaac ttaattacat gaaactaatt aaatacaaag agatgtccaa   8700
aagctcagat aaaatccaag cagcctaaag tcgattgtac ttttcttttt tctatccaca   8760
aatacaacca acaacaacca acaacaacaa caacagcagc aaccacaatt taattaaaca   8820
atagtactac tctaactaca gaacttaaat agccacaagt aaatagaatt agccacagca   8880
atttaactt ataacaagat gcccaaacac aggacactca cagaaacgtt tcttcaaaac   8940
agatttgtac tcttagccac ataaccgata cgatacaata gccacttaat taggatcgat   9000
catagccaag caatagaatc agatatcaga tacaaaactc agaaccggaa acaggaaatc   9060
gtcaatcgcg aatcggaaaa aagaagcagc accaaatcga actgcaaagg caaaccccca   9120
gtatattaat aatggggaga acataatga taaaccatt ttatttcaat tattaactta   9180
taacacaaca tcaccaccac agcttcccac agtttcagtt acacaggacc accaccatag   9240
ccctaggaaa ttatattcat aattaatcaa tcaatcaatc cgtaaaacca acaacttcaa   9300
tagttataag caattggcgt caaaaaaaaa aaaagcgaaa acaaccaaaa tcttagccag   9360
gcaaagttt tgagcatatt tttcattatt tttacaacaa acaaacaaac tgatgtaagt   9420
acaattcata aaattagact ttcggtaaac tataataaag aaaatagagc agaaaataac   9480
atttttttt tgcattacat aattgctaca aaattcaaaa acaagaacg atttttagt   9540
ggaaaacaaa agccaataag caaataaaaa gaat                              9574
```

<210> SEQ ID NO 10
<211> LENGTH: 1165
<212> TYPE: PRT
<213> ORGANISM: Drosophila melanogaster

<400> SEQUENCE: 10

```
Met His Ile Ser Ser Tyr Glu Ile Ser Leu Glu Arg Val Ala Glu Glu
1               5                   10                  15

Cys Met Gly Arg Arg Gln Trp Lys His Tyr Gln Asp Lys Leu Thr Cys
                20                  25                  30

Ser His Leu Asn Ile Glu Glu Gln Pro Ile Ala Ile Ala Gly Ser
        35                  40                  45

Glu Asp Glu Pro Ser Gln Tyr Asn His Ser Ser Lys Glu Ile Ser Gln
    50                  55                  60

Ser Asn Pro Asn His Cys Lys Thr Glu Asn His Arg Leu Glu Gln Gln
65                  70                  75                  80
```

```
His Asn Gly Ser Gln Leu Leu Glu Glu Asp Ser Glu Asn Asn Gln
                85                  90                  95

Thr Ser His Asp Ser Ser Arg Thr Pro Thr Pro Gly Ala Thr Ser Thr
            100                 105                 110

Pro Ser Pro Pro Glu Pro Ile Asp Trp Arg Pro Ser Ala Lys Cys
        115                 120                 125

Asn Phe Cys Val Asn Gly Arg Leu Leu Thr Val Asn Ala Gln Gly Lys
    130                 135                 140

Leu Val Ala Glu Ser Ala Ala Thr Ala Thr Ser Ser Ser Thr Ser Asn
145                 150                 155                 160

Ser His Ile His Gln His Asp Ser Asp Ser Asn Ser Ser Ala Ser Leu
                165                 170                 175

Pro His His Ile Ser Ser Ser Ser Ser Asn Asn Asn Ser Ser Gly
            180                 185                 190

Asn Arg Ala Arg His Ile Ala Ala Ala Ser Ala Arg Ala Thr Pro Ala
            195                 200                 205

Ala Ala Thr Pro Ala Asn Ser Leu Glu Leu Tyr Lys Leu Leu Thr Gln
    210                 215                 220

Arg Ala Ala Lys Met Thr Ser Met Asp Ser Met Ala Ala Gln Leu Ala
225                 230                 235                 240

Gln Phe Ser Leu Leu Ala Asp Phe Asn Leu Ile Asn Ser Leu Ala Ser
                245                 250                 255

Gln Gln Gln Gln Gln Gln Gln Gln Ile Ala Ser Ala Val Thr Pro
            260                 265                 270

Thr Thr Ser Glu Val Ser Ala Ala Ile Ser Pro Ala Leu Lys Asp
            275                 280                 285

Thr Pro Ser Pro Ser Val Asp Ala Pro Leu Asp Leu Ser Ser Lys Pro
            290                 295                 300

Ser Pro Asn Ser Ser Ile Ser Gly Asp Val Lys Ser Val Arg Ala Cys
305                 310                 315                 320

Ala Thr Pro Thr Pro Ser Gly Arg Arg Ala Tyr Ser Glu Glu Asp Leu
                325                 330                 335

Ser Arg Ala Leu Gln Asp Val Val Ala Asn Lys Leu Asp Ala Arg Lys
            340                 345                 350

Ser Ala Ser Gln His His Glu Gln Arg Ser Ile Leu Asp Asn Arg Leu
            355                 360                 365

Phe Lys Met Lys His His Asp Gln Glu Gln Asp His Asp Gly Asp Glu
    370                 375                 380

Leu Glu Asp Ser Asn Asp Asp Ala Glu Ala Glu Val Asp Ser Asn Ala
385                 390                 395                 400

Ser Thr Pro Val Tyr Pro Ala Glu Phe Ala Arg Ala Gln Leu Arg Lys
                405                 410                 415

Leu Ser His Leu Ser Glu His Asn Gly Ser Asp Leu Gly Glu Asp Val
            420                 425                 430

Asp Arg Gly Ser Pro Lys Met Gly Arg His Pro Ala Cys Gly Asn Ala
    435                 440                 445

Ser Ala Asn Gln Gly Ala Pro Ala Ser Ile Pro Leu Asp Ala Asn Val
    450                 455                 460

Leu Leu His Thr Leu Met Leu Ala Ala Gly Ile Gly Ala Met Pro Lys
465                 470                 475                 480

Leu Asp Glu Thr Gln Thr Val Gly Asp Phe Ile Lys Gly Leu Leu Val
                485                 490                 495
```

-continued

```
Ala Asn Ser Gly Gly Ile Met Asn Glu Gly Leu Leu Asn Leu Leu Ser
             500                 505                 510

Ala Ser Gln Glu Asn Ser Asn Gly Asn Ala Ser Leu Leu Leu Gln Gln
             515                 520                 525

Gln Gln His Gln Gln His His Gln Gln His His Gln Gln Gln Gln Gln
             530                 535                 540

Gln Gln His Val Ala Ala Tyr Arg His Arg Leu Pro Lys Ser Glu Thr
545                 550                 555                 560

Pro Glu Thr Asn Ser Ser Leu Asp Pro Asn Asp Ala Ser Glu Asp Pro
             565                 570                 575

Ile Leu Lys Ile Pro Ser Phe Lys Val Ser Gly Pro Ala Ser Ser Ser
             580                 585                 590

Ser Leu Ser Pro Gly Gly Leu Val Gly Gly His His Pro Leu Asn
             595                 600                 605

Asn Asn Asn Ser Leu Ser Ile Ser Asn Asn Ser Asn His Ser Ser Asn
             610                 615                 620

Ser His Arg Asn Gly Ser Asn Arg Ser Pro His Ser Ala Ser Pro Met
625                 630                 635                 640

Leu Ala Ala Ala Val Ala Gln Gly Gly Tyr Ser Ala Gly Asn Ser Leu
             645                 650                 655

Leu Thr Ser Ser Ser Ser Ser Ile Gln Lys Met Met Ala Ser Asn Ile
             660                 665                 670

Gln Arg Gln Ile Asn Glu Gln Ser Gly Gln Glu Ser Leu Arg Asn Gly
             675                 680                 685

Asn Val Ser Asp Cys Ser Ser Asn Asn Gly Gly Ser Ser Ser Leu Gly
             690                 695                 700

Tyr Lys Lys Pro Ser Ile Ser Val Ala Lys Ile Ile Gly Gly Thr Asp
705                 710                 715                 720

Thr Ser Arg Phe Gly Ala Ser Pro Asn Leu Leu Ser Gln Gln His His
             725                 730                 735

Ser Ala His His Leu Thr His Gln Gln Gln Gln Gln Gln Leu Ser Ala
             740                 745                 750

Gln Glu Ala Leu Gly Lys Gly Thr Arg Pro Lys Arg Gly Lys Tyr Arg
             755                 760                 765

Asn Tyr Asp Arg Asp Ser Leu Val Glu Ala Val Lys Ala Val Gln Arg
             770                 775                 780

Gly Glu Met Ser Val His Arg Ala Gly Ser Tyr Tyr Gly Val Pro His
785                 790                 795                 800

Ser Thr Leu Glu Tyr Lys Val Lys Glu Arg His Leu Met Arg Pro Arg
             805                 810                 815

Lys Arg Glu Pro Lys Pro Gln Pro Asp Leu Val Gly Leu Thr Gly Pro
             820                 825                 830

Ala Asn Lys Leu Gln Leu Asp Lys Leu Lys Ala Gly Pro His Gly Gly
             835                 840                 845

Ser Lys Leu Ser Asn Ala Leu Lys Asn Gln Asn Asn Gln Ala Ala Ala
             850                 855                 860

Ala Ala Ala Ala Ala Ala Ala Ala Ala Ala Ala Thr Pro Asn Gly
865                 870                 875                 880

Leu Lys Leu Pro Leu Phe Glu Ala Gly Pro Gln Ala Leu Ser Phe Gln
             885                 890                 895

Pro Asn Met Phe Trp Pro Gln Thr Asn Ala Thr Asn Ala Tyr Gly Leu
             900                 905                 910

Asp Phe Asn Arg Ile Thr Glu Ala Met Arg Asn Pro Gln Ala Ser Asn
```

```
                915                 920                 925
His His Gly Leu Met Lys Ser Ala Gln Asp Met Val Glu Asn Val Tyr
        930                 935                 940

Asp Gly Ile Ile Arg Lys Thr Leu Gln Ala Ser Glu Gly Asn Gly Ser
945                 950                 955                 960

Ala Ala Gly Asn Gly Ser Asn Gly Ser Asn Gly Asn Gly His Gly His
                965                 970                 975

Gly His Gly His Gly His Ala Leu Leu Asp Gln Leu Leu Val Lys Lys
            980                 985                 990

Thr Pro Leu Pro Phe Thr Asn His Arg Asn Asn Asp Tyr Ala Ala Thr
        995                 1000                1005

Cys Ser Ser Ala Ser Gly Glu Ser Val Lys Arg Ser Gly Ser Pro
    1010                1015                1020

Met Gly Asn Tyr Ala Asp Ile Lys Arg Glu Arg Leu Ser Ala Asp
    1025                1030                1035

Ser Gly Gly Ser Ser Asp Glu His Ser Ala Ser His Ile Asn
    1040                1045                1050

Asn Asn Asn Ser Asp Leu Ala His Asn Lys Asn Lys Ser Gly Gly
    1055                1060                1065

Gly Gly Gly Gly Gly Asn Gly Gln Thr Asn Gly Asn Gly Arg
    1070                1075                1080

Ser Ser Arg Met Thr Ser Arg Asp Asp Ser Glu Thr Asp Ala Ser
    1085                1090                1095

Ser Phe Lys Ser Gly Glu Asn Gly Gly Gln Gln Asn His Lys Met
    1100                1105                1110

Met Asp Leu Asn Gly Gly Ser Ser Ser Ser Ser His Ile Lys Cys
    1115                1120                1125

Glu Ser Glu Ala Ala Thr Gly His His Ser Pro Gly His His Thr
    1130                1135                1140

Thr Ser Ile Leu His Glu Lys Leu Ala Gln Ile Lys Ala Glu Gln
    1145                1150                1155

Val Asp Gln Ala Asp Gln Leu
    1160                1165

<210> SEQ ID NO 11
<211> LENGTH: 1221
<212> TYPE: PRT
<213> ORGANISM: Drosophila melanogaster

<400> SEQUENCE: 11

Met His Ile Ser Ser Tyr Glu Ile Ser Leu Glu Arg Val Ala Glu Glu
1               5                   10                  15

Cys Met Gly Arg Arg Gln Trp Lys His Tyr Gln Asp Lys Leu Thr Cys
            20                  25                  30

Ser His Leu Asn Ile Glu Glu Gln Gln Pro Ile Ala Ile Ala Gly Ser
        35                  40                  45

Glu Asp Glu Pro Ser Gln Tyr Asn His Ser Ser Lys Glu Ile Ser Gln
50                  55                  60

Ser Asn Pro Asn His Cys Lys Thr Glu Asn His Arg Leu Glu Gln Gln
65                  70                  75                  80

His Asn Gly Ser Gln Leu Leu Glu Glu Asp Ser Glu Asn Asn Gln
                85                  90                  95

Thr Ser His Asp Ser Ser Arg Thr Pro Thr Pro Gly Ala Thr Ser Thr
            100                 105                 110
```

```
Pro Ser Pro Pro Glu Pro Ile Asp Trp Arg Pro Ser Ala Lys Cys
        115                 120                 125

Asn Phe Cys Val Asn Gly Arg Leu Leu Thr Val Asn Ala Gln Gly Lys
        130                 135                 140

Leu Val Ala Glu Ser Ala Ala Thr Ala Thr Ser Ser Thr Ser Asn
145                 150                 155                 160

Ser His Ile His Gln His Asp Ser Asp Ser Asn Ser Ser Ala Ser Leu
                    165                 170                 175

Pro His His Ile Ser Ser Ser Ser Ser Asn Asn Asn Ser Ser Gly
        180                 185                 190

Asn Arg Ala Arg His Ile Ala Ala Ala Ser Ala Arg Ala Thr Pro Ala
        195                 200                 205

Ala Ala Thr Pro Ala Asn Ser Leu Glu Leu Tyr Lys Leu Leu Thr Gln
    210                 215                 220

Arg Ala Ala Lys Met Thr Ser Met Asp Ser Met Ala Ala Gln Leu Ala
225                 230                 235                 240

Gln Phe Ser Leu Leu Ala Asp Phe Asn Leu Ile Asn Ser Leu Ala Ser
                245                 250                 255

Gln Gln Gln Gln Gln Gln Gln Gln Ile Ala Ser Ala Val Thr Pro
        260                 265                 270

Thr Thr Ser Glu Val Ser Ala Ala Ile Ser Pro Ala Leu Lys Asp
        275                 280                 285

Thr Pro Ser Pro Ser Val Asp Ala Pro Leu Asp Leu Ser Ser Lys Pro
    290                 295                 300

Ser Pro Asn Ser Ser Ile Ser Gly Asp Val Lys Ser Val Arg Ala Cys
305                 310                 315                 320

Ala Thr Pro Thr Pro Ser Gly Arg Arg Ala Tyr Ser Glu Glu Asp Leu
                325                 330                 335

Ser Arg Ala Leu Gln Asp Val Val Ala Asn Lys Leu Asp Ala Arg Lys
        340                 345                 350

Ser Ala Ser Gln His His Glu Gln Arg Ser Ile Leu Asp Asn Arg Leu
        355                 360                 365

Phe Lys Met Lys His His Asp Gln Glu Gln Asp His Asp Gly Asp Glu
    370                 375                 380

Leu Glu Asp Ser Asn Asp Asp Ala Glu Ala Glu Val Asp Ser Asn Ala
385                 390                 395                 400

Ser Thr Pro Val Tyr Pro Ala Glu Phe Ala Arg Ala Gln Leu Arg Lys
                405                 410                 415

Leu Ser His Leu Ser Glu His Asn Gly Ser Asp Leu Gly Glu Asp Val
        420                 425                 430

Asp Arg Gly Ser Pro Lys Met Gly Arg His Pro Ala Cys Gly Asn Ala
        435                 440                 445

Ser Ala Asn Gln Gly Ala Pro Ala Ser Ile Pro Leu Asp Ala Asn Val
    450                 455                 460

Leu Leu His Thr Leu Met Leu Ala Ala Gly Ile Gly Ala Met Pro Lys
465                 470                 475                 480

Leu Asp Glu Thr Gln Thr Val Gly Asp Phe Ile Lys Gly Leu Leu Val
                485                 490                 495

Ala Asn Ser Gly Gly Ile Met Asn Glu Gly Leu Leu Asn Leu Leu Ser
            500                 505                 510

Ala Ser Gln Glu Asn Ser Asn Gly Asn Ala Ser Leu Leu Leu Gln Gln
        515                 520                 525

Gln Gln His Gln Gln His His Gln Gln His His Gln Gln Gln Gln
```

-continued

```
                530                 535                 540
Gln Gln His Val Ala Ala Tyr Arg His Arg Leu Pro Lys Ser Glu Thr
545                 550                 555                 560

Pro Glu Thr Asn Ser Ser Leu Asp Pro Asn Asp Ala Ser Glu Asp Pro
                565                 570                 575

Ile Leu Lys Ile Pro Ser Phe Lys Val Ser Gly Pro Ala Ser Ser Ser
                580                 585                 590

Ser Leu Ser Pro Gly Gly Leu Val Gly Gly His His Pro Leu Asn
    595                 600                 605

Asn Asn Asn Ser Leu Ser Ile Ser Asn Asn Ser Asn His Ser Ser Asn
610                 615                 620

Ser His Arg Asn Gly Ser Asn Arg Ser Pro His Ser Ala Ser Pro Met
625                 630                 635                 640

Leu Ala Ala Ala Val Ala Gln Gly Gly Tyr Ser Ala Gly Asn Ser Leu
                645                 650                 655

Leu Thr Ser Ser Ser Ser Ile Gln Lys Met Met Ala Ser Asn Ile
                660                 665                 670

Gln Arg Gln Ile Asn Glu Gln Ser Gly Gln Glu Ser Leu Arg Asn Gly
            675                 680                 685

Asn Val Ser Asp Cys Ser Ser Asn Gly Gly Ser Ser Ser Leu Gly
690                 695                 700

Tyr Lys Lys Pro Ser Ile Ser Val Ala Lys Ile Ile Gly Gly Thr Asp
705                 710                 715                 720

Thr Ser Arg Phe Gly Ala Ser Pro Asn Leu Leu Ser Gln Gln His His
                725                 730                 735

Ser Ala His His Leu Thr His Gln Gln Gln Gln Gln Leu Ser Ala
                740                 745                 750

Gln Glu Ala Leu Gly Lys Gly Thr Arg Pro Lys Arg Gly Lys Tyr Arg
            755                 760                 765

Asn Tyr Asp Arg Asp Ser Leu Trp Arg Arg Ser Arg Cys Arg Glu
            770                 775                 780

Leu Lys Cys Arg Phe Ile Glu Arg Val Ala Thr Met Arg Thr Ala Phe
785                 790                 795                 800

His Thr Gly Val Gln Gly Gln Gly Thr Ser Pro Asp Ala Thr Ala Gln
                805                 810                 815

Ala Arg Ala Gln Ala Ala Ala Arg Ser Arg Arg Pro Asp Arg Thr Ser
                820                 825                 830

Gln Gln Ala Ala Ala Gly Gln Thr Glu Gly Gly Thr Thr Trp Trp Leu
                835                 840                 845

Gln Ala Glu Gln Cys Pro Gln Glu Pro Lys Gln Ser Gly Gly Cys Gly
850                 855                 860

Gly Gly Gly Gly Ser Ser Ser Gly Arg Cys His Ala Gln Arg Pro
865                 870                 875                 880

Glu Thr Ala Pro Phe Arg Gly Gly Ser Thr Gly Val Ile Leu Ser Ala
                885                 890                 895

Glu His Val Leu Ala Pro Asp Glu Arg His Glu Cys Leu Arg Pro Gly
                900                 905                 910

Leu Gln Ser His His Gly Gly Asp Ala Glu Phe Pro Gly Leu Gln Ser
            915                 920                 925

Pro Arg Leu Met Lys Ser Ala Gln Asp Met Val Gly Glu Arg Leu Arg
            930                 935                 940

Trp His His Gln Glu Asp Ala Ala Gly Glu Gln Gly Asn Gly Ser Ala
945                 950                 955                 960
```

Ala Gly Asn Gly Ser Asn Gly Ser Asn Gly His Gly His Gly
                965                 970                 975
His Gly His Gly His Ala Leu Leu Asp Gln Leu Leu Val Lys Lys Thr
            980                 985                 990
Pro Leu Pro Phe Thr Asn His Arg  Asn Asn Asp Tyr Val  Val Thr Cys
        995                 1000                 1005
Ser Ser  Ala Ser Gly Glu Ser  Val Lys Arg Ser Gly  Ser Pro Met
    1010                 1015                 1020
Gly Asn  Tyr Ala Asp Ile Lys  Arg Glu Ala Leu Ser  Ala Asp Ser
    1025                 1030                 1035
Gly Gly  Ser Ser Asp Glu Glu  His Ser Ala Ser His  Ile Asn Asn
    1040                 1045                 1050
Asn Asn  Ser Asp Leu Ala His  Asn Lys Asn Lys Ser  Gly Gly Gly
    1055                 1060                 1065
Gly Gly  Gly Gly Asn Gly Gln  Thr Asn Gly Asn Gly  Arg Ser Ser
    1070                 1075                 1080
Arg Met  Thr Ser Arg Asp Asp  Ser Glu Thr Asp Ala  Ser Ser Phe
    1085                 1090                 1095
Lys Ser  Gly Glu Asn Gly Gly  Gln Gln Asn His Lys  Met Met Asp
    1100                 1105                 1110
Leu Asn  Gly Gly Arg Ala Ala  Ala Val Thr Ser Ser  Ala Asn Arg
    1115                 1120                 1125
Arg Arg  Pro Pro Asp Ile Thr  Val Leu Asp Thr Thr  Pro Arg Pro
    1130                 1135                 1140
Tyr Cys  Thr Arg Ser Trp Ser  Arg Ser Arg Pro Ser  Lys Trp Thr
    1145                 1150                 1155
Arg Arg  Phe Ser Tyr Trp Ser  Ser Arg Trp Thr Arg  Ile Gln Arg
    1160                 1165                 1170
Ser Pro  Trp His Arg Trp Ser  Pro Thr Thr Thr Val  Ser Trp Arg
    1175                 1180                 1185
Arg Glu  Gly Glu His Gln Ile  Lys Pro Arg Phe Leu  Val Val Pro
    1190                 1195                 1200
Tyr Lys  Ser Leu Asn Arg Ile  Ile Tyr Ile Tyr Ile  Tyr Ile Tyr
    1205                 1210                 1215
Ile Leu  Leu
    1220

<210> SEQ ID NO 12
<211> LENGTH: 9567
<212> TYPE: DNA
<213> ORGANISM: Drosophila melanogaster

<400> SEQUENCE: 12
gttgctgtcg ataatttact ctgtgctcca catatatata tatatatata tatatatata      60
ttataaataa aaaccaacca atagcccaaa aaaaaaaaag aaatgaaaaa tccgcatcaa     120 cataaaaat ctgcctgcat ttttgccttt tgtgtgagct gcccagcaga acgagagaag      180 cactttatt gtatataaaa attatataca tcgccaggag gagctgcagc aacccactcc     240
aagccaggtt gccacgtcct gagctgctgt aagttctccg cagcagctgc agcagcatca     300
gcatcgcagc agcatcagca gcagcgcaca atccgccgca gcatcaattt ggcttttggg     360
cagagataat ttaagacaaa tatatgtgat gctatgcaca tcagcagcta tgaaatatcc     420
ctagaacgcg ttgctgaaga atgtatgggt cgcaggcaat ggaaacatta tcaagacaaa     480

-continued

```
ctgacgtgca gccacttgaa tatcgaggag caacagccca tagcaatagc cggttccgag      540
gacgagccat cgcaatacaa ccacagcagc aaggagatca gccagagcaa tcccaaccac      600
tgtaagacag agaaccaccg tctggagcag caacacaacg gcagccagct attggaagaa      660
gaagattctg agaacaacca acatcacac gattcatcac gtacaccaac accgggagcc       720
accagtacac catcaccacc gccagaaccc atcgattgga gaccgtcggc caagtgcaac      780
ttctgtgtta acggtcgcct gctaacggtt aacgcccagg gcaagttggt ggccgagtca      840
gcagcaactg ccactagtag tagcactagt aatagtcaca ttcatcagca cgacagtgac      900
agcaactcga gtgcatcact gccccaccac atcagcagca gcagcagcag caacaacaat      960
agcagtggca acagggcacg ccacattgct gctgcaagtg caagagcaac accagcagcg     1020
gccacacccg ccaactccct tgaactctac aagctgctga cccagcgggc agccaaaatg     1080
acatcgatgg actcgatggc cgcccagctg gcgcaattct cactgctggc cgacttcaat     1140
ctgatcaact cgctggccag ccaacagcag cagcagcagc agcaacagat cgctagtgcg     1200
gtaacgccaa ctacctcaga agtatctgca gccgcaatca gtcccgcact caaagataca     1260
cccagtccca gtgtggatgc accgctcgat cttagcagca accatcgcc gaactcatcg       1320 attagcggcg atgtgaagtc cgtcagagcc tgtgccacgc ccacgccgtc gggaagaagg     1380
gcgtacagtg aagaggatct gagccgggcc ctacaggatg tggtggccaa caagctagat     1440
gcccggaaat cggctagcca gcaccatgag cagcgctcca ttctggacaa ccggctgttc     1500
aagatgaaac accatgacca ggagcaggat catgatggcg acgagctcga ggactccaac     1560
gatgatgctg aggcggaagt ggacagcaat gcgtcgacac cggtgtatcc ggcagagttt     1620
gcaagggcac aactgcgcaa actgagccac ctgtccgagc acaatggcag cgatctgggc     1680
gaggatgtgg atcgtggatc gccgaaaatg gggcgacatc cggcctgtgg caatgccagt     1740
gccaatcagg gcgcaccggc atccattccg ctggatgcca atgtcctgct gcacactctg     1800
atgctggctg ctgggattgg tgcaatgccg aagctggatg aaacgcaaac ggtgggcgac     1860
tttatcaagg gtctgctggt ggccaacagt ggtggcataa tgaacgaggg actgctaaat     1920
ctgctgtccg ccagtcagga gaacagcaat ggcaatgcct cgctgctgct gcaacagcaa     1980
cagcatcagc aacaccatca gcaacaccat cagcagcagc agcagcagca acatgtcgcc     2040
gcctaccggc atcgcctgcc caagtcggag actccggaaa cgaactcctc gttggatccg     2100
aacgatgcca gcgaggatcc catactgaag attccgtcct tcaaggtcag cggtccggcc     2160
agcagcagca gcctgtcgcc gggcggactg gttggtggtc accaccatcc gctgaacaac     2220
aacaacagcc tcagcatcag caacaacagc aaccacagca gcaacagcca tcggaacggc     2280
agcaatcgca gcccgcattc cgcatcgccc atgctggccg cggccgtggc ccaaggtggc     2340
tactccgccg gcaacagttt gctgacctca tcctcgtcta gcatacagaa gatgatggcc     2400
agcaatatcc agcgccagat caacgaacag agtggccagg agagtctcag gaacggaaat     2460
gttagcgatt gcagcagcaa caatggcggc tcctcctcgc tgggatacaa gaagccgagc     2520
atttcggtgg ccaagatcat tggcggaacg gacacctcac ggttcggagc ctcgcccaat     2580
ctgctgtccc aacagcacca ttcggctcac cacctgaccc accagcaaca gcagcaacag     2640 ctgacgccc aggaggcatt gggcaaggga acgcgaccaa agaggggcaa gtatcgcaac       2700
tatgaccgcg acagtttgtg gaggcggtca aggcggtgca gagagttgaa atgtcggttc     2760
atcgagcggt tagctactat gcgtaccgca ttccacactg gagtacaagg tcaaggaacg     2820
tcacctgatg cgaccgcgca agcgagagcc caagccgcag cccgatctcg tcggcctgac     2880
```

-continued

```
cggaccagcc aacaagctgc agctggacaa actgaaggcg ggaccacatg gtggctccaa      2940
gctgagcaat gccctcaaga accaaaacaa tcaggcggct gcggcggcgg cggcggcagc      3000
agcagcagcg gccgctgcca cgcccaacgg cctgaaactg cccctttcg aggcgggtcc       3060 acaggcgtta tcctttcagc cgaacatgtt ctggccccag cgaacgcca cgaatgccta       3120 cggcctggac ttcaatcgca tcacggaggc gatgcggaat tcccaggcct ccaatcacca      3180
cggcttatga agagtgccca ggacatggtt ggagaacgtt tacgatggca tcatcaggaa      3240
gacgctgcag gtgagcaggg caatggcagt gcggcgggta atggcagcaa cggtagcaat      3300
ggcaacgggc atgggcacgg gcatggccat ggacacgccc tgctcgatca gctgctggtg      3360
aagaagaccc ccttgccgtt caccaaccat cggaacaatg actacgtcgt cacctgttcg      3420
agtgccagcg gggagagcgt aaagcggtcg ggcagtccca tgggcaacta tgcagacatc      3480
aagcgggagg ccctgagcgc cgacagcggc ggcagcagcg atgaggagca ctcggccagc      3540
cacatcaaca acaacaacag cgatttggcg cacaacaaga acaagagcgg cggcggcggc      3600
ggcggcggca atggccagac caatgggaac ggcaggagca gccggatgac gtcgcgggat      3660
gattccgaaa cggatgccag cagctttaag agcggcgaaa atggcggcca gcaaaaccac      3720
aaaatgatgg atctcaatgg cggcagagca gcagcagtca catcaagtgc gaatcggagg      3780
cggccaccgg acatcacagt cctggacacc acaccacgtc catactgcac gagaagctgg      3840
tccagatcaa ggccgagcaa gtggaccagg cggttcagtt attggagcag ccgatggacg      3900
cgaatccagc gttcgccttg gcaccgttgg tcgcccacta ctacagtttc ttggcggagg      3960 gaggggggaac accaaattaa gccacgtttt ttagtagtac catacaaatc actaaataga     4020
attatatata tatatatata tatatatatt ctttttataat attttatgcc agccagctga    4080
ccgatgtgcg tggtaaatgt gcgctagtct tagttaaatg tgtaatcaac tgcatagggg      4140
aaaaacaaaa ccacaggaaa tcataaataa caacaaacaa acaaacaaac aaaaataaca      4200
aaaataacaa gaaccgcaag caaagaaaca tacatttgtg ccccggagtg tacgatgtat      4260 attttttgttt cgttttgaca atcgacaaat aggcattctc ttgtacaaac tttcttaaaa      4320
gctaacaaca aaacaaatct aaaaccttaa gaccaaaaaa aacaaaaaat gaaaaaaaac      4380
gaatactgag caaaaaccaa gaaccatttt catttttgcat ttcgtttcga accgcattttt    4440 tgtgttgagc atattttttta ctgaacagta aatgaaacag tccaatggga aaatatatgt     4500
atagcagaaa tatatagcac ttacaagcca acaacttaat cgacttctgt tttggtcagg      4560
tttctggacc ttgagctgcg attttcgcac attccataag atactcttat gttccatata      4620
attgtagttt tcatacgcaa atttctagag cagttagagc cgcagctcag acagggccaa      4680
aaccaaaaaa aatgaccagg cagttgtcct cgacatagac acaatgagta taggccaaca      4740
acagcaacta caacagcaac aataactaca gcaaagagac cataacaaca acaacaacaa      4800
caacaacaac agtaacaacc ataacaagca acaacaacag caatatccga tcaataacaa      4860
caaccaacaa aacaagcaat aataatacaa gactctacaa tacaaagaaa tgaaacattg      4920
aaatagcaaa attcaaaatt caaaatatata aaccgaaaaa ccacaatcaa aaaccaaaa      4980 caaaattatc cacaaaaatt caaccatttt ttatgatttc caaaggagg aaaatacaaa       5040 acggaaatcc aattaaccaa agctgccttc acatttacca attaaataaa ttagtaagca      5100
aagcgagaca aagcacacaa aataataatt caaatgaaac gcaaacgcag agtaaaaagc      5160
aagaaaatca aacaatttcc gaaatatcag tcccaaatta cattttttatt ttgaaaaatt    5220
```

```
ccaaaaccta agaatacaaa atattacacc ccaaaacatt caaaattatt ttcattcgga    5280
aaaaaatttc acacatattc aaataaagta atcaaaatta aagtgtttcg gtgttaaaaa    5340
aaaataaaag ggaaaattac cgaaatatat atatctgtgt ttagacttta aaacggaaat    5400
ttgaaaacaa aatttcaaga tttcggctta aaagtaaaaa gagagacaaa aaaaaaacaa    5460
aacaaatgtt tgagaacaca catttcatgt acagtcgcct aaccaccaaa agtaagaaag    5520
cataaatata taaagacttt atattactat ataccatatg atatatattt gtatatttat    5580
gtatgtgtgt gtcttcatca ctacgcgtat accctcaaac caaacacatg atcattttga    5640
gcaactaaat atatttaaat gtacttatac actctacaca ctcttttaca ggagagcaaa    5700
acatatttac acagttaaac ccccccaat ccaaatcttt ggccctcctt tcgacgtatc     5760
tacatttcgt ttgactttga aattctatct atgggtaaac aactactaac taaatgtctg    5820
cgtaaatgaa aatagatggc caattatata aatgtccctta aaaacacata ttttgtgtgc   5880
tagctagtaa gtgtcaaagg aaaaacaaaa aaaccataca aaaacgatat acaatatatt    5940
taaatgatta tgagatggtg aaaattgtcg gaaatatttg aaaatattta gcgaattata    6000
atacaagaaa cagtcaaagg tatggcaagg aaaattgtgg aaaatagcaa gcgaaatgcg    6060
tttaataatt atattgaaat catttaaagg catttaatat atttatcatt tccacgatgc    6120
gattgataaa acagtattta ttggctaatc tccccaatta catttgatgt gcataaatgt    6180
tgtggtttag aatcaaaatc aaaggtacaa aattaaaagt taaggcttaa aaatgtaaaa    6240
aaaaaattta atacaattat gaattttggt ataatagcgg agagttctgc gaacctaaag    6300
aaattcaaaa tgtttattat atgaaaaatg gaaaatgga aggaaaaata ggcgagagta     6360
gataaagaat ggatggaaat aaatcaaaaa gtatttattg ctaatttaat tatatttgaa    6420
gtatacatac atatttatta tatacataca tatatattag acaccctgtc tgtgattaat    6480
aatccaaaat tttgaagagc attttctgaa ataacgttgg ctaagcatat gcgaaaagac    6540
aaaaccaatg gataaagtaa cacacaccca tgtaaagaaa ttgtagacag atcggataaa    6600
acgaaactaa accaagcaca agctaatggc ccaaatgcag ttggccccga aaatcgagcg    6660
ctgcatttgg ccaagagaat tcttaagct acggcacaca tcactgaaaa caaaaactga    6720
aaactgaata ctgaatactg cgaataggaa acagtaagca gaagacaaga tcgatggtac    6780
tgttcagaac atatatagtt gtatatattt tggaataatg tttaccagtt caagtcaaaa    6840 ttaaaggaa aaaaaatgca aagtctttta taatgcaaaa ttatacaaag aaaaattaca    6900
atttcgcaac gctaaaaaat gaaaaacgaa aatattgatg taaaaagaat gaaaatcaaa    6960
cttaaaataa taaacaagat aaagtgcaat tatacggttt aaataagcaa atttaagaaa    7020
caaacgttat aaacaaaaac acaaacatgt taaaacaatg aaaatatttc gaagcaagtt    7080
tagctacaaa ttccaaggca actgataatg acaagaacca tttacaagaa aaaccaagac    7140
agcaaagtac agtgcgtttc atgactcgca aatacgggca atagaatact agtttttcat    7200
tgcccatgga gaactgaaac gcactttggc cctcacttca tattgatagg gtaatcggat    7260
ccaaaatctg taaccaaat tttgggatca gcgattaaaa ccttaacgga agttcataac     7320
tgcagaaaaa aaaagtcgaa agtcgaaatg tcaacctagt ggtagttcga aacacaaaaa    7380
caaaacaaac caatcgagtg taattgagtg acagcttgag aatgttgaat tgtatagaat    7440
ttttgcttgt gcacctggtc gaggggggccg tggttgcgcc ccctttttgg tttctaggtg    7500
aacaggcgaa aacgctcagg tacgtgtttt attttttcgga gagaaacaag attgattacc    7560
catacattac ttattctttg ttttactaca acataatagt taatatttgt ataaaaaaaa    7620
```

-continued

```
aagacgacga tggcgagaag ggaaaaccag ctaaaaaaat tgatatattc ataatataga    7680
attgttttaa atggtttgag agcgaaaaat attgagggtt tctagcgtgc ttcatgaaat    7740
tgctcatatt tgtgtataaa accttatttg ttcaatgcga atcaaaattt gctgaatata    7800
agtgcatata tatataatta gagtttattt ttcggtttag ttaagcgcat acaatgatta    7860
cgatttaaat aattattatt agttatgacc taatagtagg caaatcaaaa tttcttcaca    7920
taaaacaatc aacttctact ttcaaataat ttctagacgt atgtaactat aggttattat    7980
tctattatta tacggcctaa aactatttag cgcgttgtta gactcgattt atggtttgta    8040
catattagac aacatttta tggtattctc ctcttttttt attattacta gcattattac     8100
tccctatttt aattgacttc ttaaatgggc aacatcattt tgaactatag tgcaattgtt    8160
tcaaacaaaa ccaagcaacc aacaacaaat atattaacat taaagattaa tataatttac    8220
aagctttctt tgccgatgcc aagaaggatg aataacgcat atgtctaccg tatggatcga    8280
aaatcaaaaa tcattttaag tgcacataac tctttaaaat agcaattaga ctacgactag    8340
gttttttccat tattatgcgc acgcttcagt ccaaaaaaaa aaaaattgaa attcttcaca   8400
ttctcattca catgctcagt tcgagacatc acaatcacaa gccagaaaaa gaaaactcaa    8460
aacttttcac ctaagttcaa cttgagcgac cgcaacaact caagatcagc aaagatcaca    8520
agcgaaaatt gctaagaaac aatagcccag acgtgataac aaccacaaaa tagccacaac    8580
aatagcccaa aaataattga aacaaaaatt gattaaaagc caaaaaaaaa ataaaaaagc    8640
aaataataag aacttaatta catgaaacta attaaataca aagagatgtc caaaagctca    8700
gataaaatcc aagcagccta aagtcgattg tactttctt ttttctatcc acaaatacaa     8760
ccaacaacaa ccaacaacaa caacaacagc agcaaccaca atttaattaa acaatagtac    8820
tactctaact acagaactta aatagccaca agtaaataga attagccaca gcaatttaac    8880
tttataacaa gatgcccaaa cacaggacac tcacagaaac gtttcttcaa aacagatttg    8940
tactcttagc cacataaccg atacgataca atagccactt aattaggatc gatcatagcc    9000
aagcaataga atcagatatc agatacaaaa ctcagaaccg gaaacaggaa atcgtcaatc    9060
gcgaatcgga aaaagaagc agcaccaaat cgaactgcaa aggcaaaacc ccagtatatt     9120
ataatggggg agaaacataa tgataaacca tttttatttc aattattaac ttataacaca    9180
acatcaccac cacagcttcc cacagtttca gttacacagg accaccacca tagccctagg    9240
aaattatatt cataattaat caatcaatca atccgtaaaa ccaacaactt caatagttat    9300
aagcaattgg cgtcaaaaaa aaaaaaagcg aaaacaacca aaatcttagc caggcaaaag    9360
ttttgagcat atttttcatt atttttacaa caaacaaaca aactgatgta agtacaattc    9420
ataaaattag actttcggta aactataata aagaaaatag agcagaaaat aacattttt     9480
ttttgcatta cataattgct acaaaattca aaaacaaaga acgattttt agtggaaaac     9540
aaaagccaat aagcaaataa aaagaat                                         9567
```

GENES REGULATING PROGRAMMED CELL DEATH

CROSS REFERENCE TO RELATED APPLICATIONS

This application claims the benefit from U.S. Provisional Application Ser. No. 60/243,865, filed Oct. 27, 2000.

GOVERNMENT RIGHTS IN INVENTION

Some aspects of the invention disclosed in this application were supported by the United States government, National Institute of Health Grant No. GM 59136. Accordingly, the U.S. Government has certain rights in the invention hereof.

BACKGROUND OF THE INVENTION

1. Field of the Invention

The present invention relates generally to apoptosis or programmed cell death, and more particularly, to amino acid sequences of proteins that are associated with apoptosis and the use of these proteins in the diagnosis, prevention and treatment of disorders associated with abnormal cell proliferation and apoptosis.

2. Background of the Related Art

Programmed cell death or apoptosis plays a critical role during animal development by functioning in the destruction of unneeded cells and tissues. The term programmed death was established to distinguish physiological or genetic-regulated cell death from necrotic cell destruction. Genetically regulated cell death is an integral component of normal development, and is used in processes such as, limb formation and nervous system remodeling. Cell death is also involved in removal of abnormal cells during development, including those during tumor genesis.

It has now become clear that disturbances in programmed cell death, which prevent or delay normal cell turnover, can be just as important to the pathogenesis of diseases as known abnormalities in the regulation of proliferation and the cell cycle. Like cell division, which is controlled through complex interactions between cell cycle regulatory proteins, programmed cell death is similarly regulated under normal circumstances by the interaction of gene products that either induce or inhibit cell death.

The stimuli that regulate the function of these apoptosis gene products include both extracellular and intracellular signals. Either the presence or the removal of a particular stimulus can be sufficient to evoke a positive or negative apoptosis signal. For example, physiological stimuli that prevent or inhibit apoptosis include growth factors, extracellular matrix, CD40 ligand, viral gene products, neutral amino acids, zinc, estrogen and androgens. In contrast, stimuli that promote apoptosis include growth factors such as tumor necrosis factor (TNF), Fas and transforming growth factor β (TGF β). Other stimuli that promote apoptosis include, for example, neurotransmitters, growth factor withdrawal, loss of extracellular matrix attachment, intracellular calcium and glucocorticoids. Although apoptosis is mediated by diverse signals and complex interactions of cellular gene products, the results of these interactions ultimately feed into a cell death pathway that is evolutionarily conserved between humans and invertebrates.

Several gene products that modulate the apoptotic process have now been identified. Although these products can be generally separated into two basic categories, gene products from each category can function to either inhibit or induce programmed cell death. One family of gene products is related to the protein Bcl-2, which inhibits apoptosis when overexpressed in cells. A second family of gene products, the aspartate-specific cysteine proteases (ASCPs), are genetically related to the ced-3 gene product, which was initially shown to be required for programmed cell death in the roundworm, *C. elegans* (Ellis et al., 1991)

A series of elegant genetic studies of programmed cell death in the worm *C. elegans* led to the isolation of the ced-3, ced-4 and ced-9 genes. Ced-3 is homologous to the mammalian family of caspases, which upon proteolytic activation are critical effectors of the programmed cell death signaling pathway (Cryns and Yuan, 1998). CED-4 is homologous to mammalian Apaf-1, which activates caspases in the presence of cytochrome c and dATP. CED-9 is a member of the Bcl-2 family of cell death regulators and found to represses the apoptosis of many different cells in the nematode development.

Apoptosis maintains tissue homeostasis in a range of physiological processes such as embryonic development, immune cell regulation and normal cellular turnover. Therefore, the dysfunction or loss of regulated apoptosis can lead to a variety of pathological disease states. Clearly, there is a need for factors that are useful for inducing apoptosis for therapeutic purposes, for example, as an antiviral agent, an anti-tumor agent to control embryonic development and tissue homeostasis, and the roles of such factors in dysfunction and disease. Further, there is a clear need for factors that are useful for reducing or halting apoptosis for therapeutic purposes, for example, to treat diseases caused or associated with apoptosis, such as Alzheimer's disease, Parkinson's disease, rheumatoid arthritis, chronic inflammation, acute inflammation, AIDs, degenerative liver disease and the like. Treatments that are specifically designed to modulate the apoptotic pathways in these and other pathological conditions can change the natural progression of many of these diseases.

Genetic screens in *Drosophilia* have revealed three cell death inducer genes: reaper (rpr) head involution defective (hid) and grim. The function of these genes is required for virtually all programmed cell death during embryogenesis. Ectopic expression of each of these genes is also sufficient to induce caspase-dependent programmed cell death in a wide range of cell types. Although vertebrates homologs of rpr, hid and grim have not yet been identified, expression of each of these genes is sufficient to induce apoptosis in mammalian cells (McCarthy and Dixit, 1998; Haining et al., 1999) suggesting that the downstream death pathway may be conserved between flies and mammals.

The similarity between vertebrate and invertebrate cell death pathways establishes *Drosophila* as a valuable model system for genetics studies of the regulation of apoptosis in humans and thus could be the vehicle to identify new apoptotic genes and their gene products to modulate apoptosis for the therapeutic treatment of human diseases.

SUMMARY OF THE INVENTION

The present invention relates to identifying novel proteins that possess apoptosis activity by homology between the amino acid sequence of SEQ ID NO: 1 and other amino acid sequences of proteins in both vertebrates and invertebrates. Included in the homologous amino acid sequences that possess apoptosis activity are SEQ ID NO: 2, SEQ ID NO: 3, SEQ ID NO: 4, SEQ ID NO: 5 and SEQ ID NO: 8.

The present invention also relates to a protein associated with apoptosis having at least 60% homology over the complete sequence of the amino acid sequence of SEQ ID NO: 1.

The present invention further relates to identifying a modulator of apoptosis to ameliorate the effects of Alzheimer's disease, cancer, Parkinson's disease, rheumatoid arthritis, chronic inflammation, acute inflammation, AIDs, and degenerative liver disease.

The present invention also provides a method for preventing or treating a disorder associated with a decrease in apoptosis, the method comprising:

administering to a subject in need of such treatment an effective amount of a pharmaceutical composition comprising a apoptotically active protein having an amino acid sequence (i) of SEQ ID NO: 1 or (ii) with at least 60% homology to SEQ ID NO: 1.7.

The homologous amino acid sequence comprising 60% amino acid identity over the complete sequence of SEQ ID NO: 1 is selected from the group consisting of SEQ ID NO 2, SEQ ID NO 3, SEQ ID NO 4, SEQ ID NO: 5 and SEQ ID NO 8.

This invention further provides for a purified and isolated nucleic acid molecule encoding a mutated protein with homology to SEQ ID NO: 1.

The present invention also provides a method for detecting a polynucleotide that encodes an apoptopic protein having at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8 in a biological test sample containing nucleic acids, the method comprising the steps of:

(a) mixing at least a fragment of a complement of the polynucleotide sequence encoding at least a fragment of a protein having at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8 with the biological test sample containing nucleic acids, to form a resulting mixture;

(b) subjecting the mixture to conditions such that hybridization will occur between the biological test sample and the complement of the polynucleotide sequence encoding at least a fragment of a protein having at least one amino acid sequence selected from the group consisting of SEQ ID NO: 1, SEQ ID NO: 2, SEQ ID NO: 3, SEQ ID NO: 4, SEQ ID NO:5 and SEQ ID NO: 8; and (c) detecting hybridization complexes in the mixture subjected to hybridization conditions, wherein the presence of a hybridization complex correlates with the presence of a polynucleotide encoding a protein having at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8 in the biological test sample.

Further, the nucleic acids of the biological test sample may be amplified by a polymerase chain reaction prior to hybridizing step.

In yet another aspect, the present invention relates to a method for screening a potential cellular apoptosis inhibiting compound for determining it utility as a therapeutic agent for treatment of diseases associated with increased programmed cell death, the method comprising:

(a) contacting a cell which expresses a protein including at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8 with the test compound; and (b) determining the level of apoptosis activity of the cell, wherein a decrease in activity identifies a compound that inhibits apoptotic activity.

In another aspect, the present invention further provides an expression vector containing at least a fragment of a polynucleotide sequence encoding a polypeptide comprising at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8.

In another aspect this expression vector is contained within a host cell and transforms the host cell to express therapeutically effective amounts of a polypeptide comprising at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8.

This invention also provides a method for producing a polypeptide comprising at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8, the method comprising:

(a) culturing a host cell containing an expression vector containing a polynucleotide sequence encoding for a polypeptide comprising at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8 under conditions suitable for the expression of the polypeptide; and (b) recovering the expressed polypeptide form the host cell line.

The present invention further relates to a purified antibody which binds to a polypeptide comprising at least one amino acid sequence selected from the group consisting of SEQ ID NO: 1, SEQ ID NO: 2, SEQ ID NO: 3, SEQ ID NO: 4, SEQ ID NO: 5 and SEQ ID NO: 8, as well as an agonist and an antagonist to the polypeptides of the present invention.

The invention also relates to a method for preventing or treating a disorder associated with decreased apoptosis comprising administering to a subject in need of such treatment a pharmaceutical composition comprising a polynucleotide sequence that encodes for a peptide comprising an amino acid sequence selected from the group consisting of SEQ ID NO: 1, SEQ ID NO: 2, SEQ ID NO: 3, SEQ ID NO: 4, SEQ ID NO: 5 and SEQ ID NO: 8 or a composition comprising a peptide comprising an amino acid sequence selected from the group consisting of SEQ ID NO: 1, SEQ ID NO: 2, SEQ ID NO: 3, SEQ ID NO: 4, SEQ ID NO: 5 and SEQ ID NO: 8.

Other features and advantages of the invention will be apparent from the following detailed description, drawings and claims.

BRIEF DESCRIPTION OF THE FIGURES

FIG. 1 shows the alignment of the amino acid domain that is conserved between *Drosophila* E93 and predicted proteins in humans, fish, mice and worms.

FIG. 2 shows the nucleotide sequence of the human E93A (A) and E93B (B) transcription units.

FIG. 4 shows the amino acid sequence of the predicted human E93 protein. The conserved amino acid domain is underlined.

DETAILED DESCRIPTION OF PREFERRED EMBODIMENTS

I. The Invention

Figure 3:
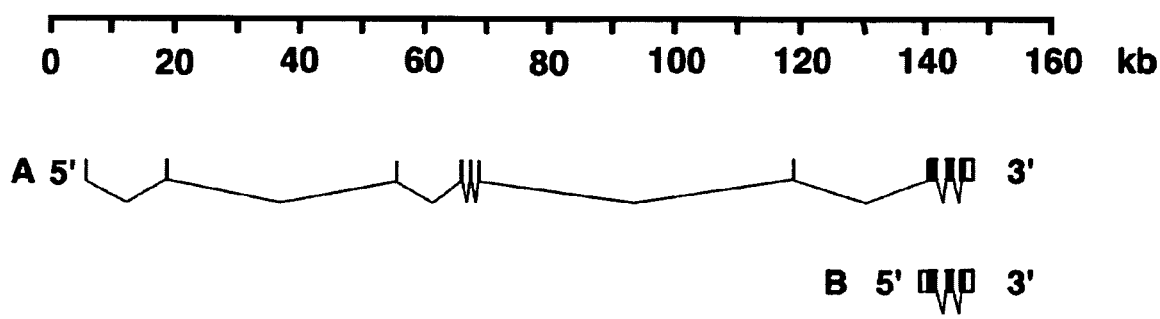
FIG. 3 shows the genomic organization of the human E93A (A) and E93B (B) transcription units. The hE93A primary transcript is greater than 140 kilobases (kb) in length, while the hE93B primary transcript is 10 kb in length.

Isolation of the correct sequence for the *Drosophila* E93 gene that encodes for a protein found to modulate apoptosis provided the tool for isolation of proteins associated with modulation of programmed cell death and the encoded proteins. The discovery of proteins with apoptosis activity can be used as agonists, antagonists, antibodies and for treating disorders related to apoptosis.

A proposed *Drosophila* E93 gene (SEQ ID NO: 12) was first identified based on its induction by the steroid 20-hydroxyecdysone (ecdysone) just prior to programmed cell death of larval salivary glands (Baehrecke and Thummel, 1995). At the time the first proposed E93 gene was isolated, no similar genes had been identified. However, subsequent to the isolation of the first proposed E93 gene an error was discovered in the original gene sequence that had a marked effect on the predicted E93 protein (SEQ ID NO: 11). Specifically, the omission of a nucleotide that changed the reading frame encoded for an amino acid sequence markedly different from that of the present invention. The amino acid residue sequence in SEQ ID NO: 11 ranging from 776 to and including 956 has since been determined to be incorrect.

The recently identified and corrected gene sequence (SEQ ID NO: 9) that encodes for a an amino acid sequence (SEQ ID NO: 10 with a different amino acid residue sequence ranging from 775 to and including 955) has provided the present inventor with a tool to identified a 53 amino acid domain in *Drosophila* E93 (SEQ ID NO: 1) that is conserved in the human *H. sapiens* (SEQ ID NO: 2), the fish *T. nigroviridis* ((SEQ ID NO: 3), the mouse *M. musculus* (SEQ ID NO: 4) and the nematode *C. elegans,* (SEQ ID NO: 5) as shown in FIG. 1.

Animals that possess mutations in E93 have defects in programmed cell death, and their salivary glands do not die (Lee and Baehrecke, 2001; Lee et al., 2000). E93 protein binds to chromosomes, and E93 mutants exhibit defects in cell death gene transcription including the caspase dronc. Furthermore, expression of E93 is sufficient to induce programmed cell death in different *Drosophila* cells types during development. Previously isolated steroid-regulated genes that function in programmed cell death also regulate cell differentiation and morphogenesis in *Drosophila* , while E93 appears to function more specifically in cell killing. Combined, these data indicate that *Drosophila* E93 regulates programmed cell death by regulating the transcription of programmed cell death genes.

The human E93 (hE93) gene has been characterized and found to include two distinct RNAs based on the isolation of related but independent cDNAs. One cDNA was isolated from a human testis (FIG. 2A) library and the other cDNA from a fetal brain (FIG. 2B) library that were obtained from Origene, Inc. These cDNAs were sequenced on both strands and are identical in most of their sequence, but possess different 5' ends. The cDNA isolated from testis encodes a 4958 base RNA that has been named hE93A, and the cDNA isolated from fetal brains encodes a 6074 base RNA that has been named hE93B. These sequences map to the same region of human chromosome 4, and are alternative transcript forms of hE93. The transcripts utilize alternative promoters and splicing, but encode identical predicted proteins. In FIG. 2A, bases 1–690 encode the hE93A-specific region and in FIG. 2B the hE93B-specific region includes bases 1–819. The remaining bases in both FIGS. 2A and 2B encode for the same polypeptide comprising a 53 amino acid domain that is conserved between *Drosophila* E93 and the human hE93 protein. Specifically, bases 1547 to 1705 in FIG. 2A and bases 2676 to 2834 in FIG. 2B are conserved with the amino acid domain of *Drosophila* E93.

In order to facilitate review of the various embodiments of the invention and provide an understanding of the various elements and constituents used in making and using the present invention, the following terms used in the invention description have the following meanings.

2. Definition

An "allele" or "allelic sequence", as used herein, is an alternative form of the gene encoding for a polypeptide comprising the any one of the amino acid sequences of SEQ ID NOs: 1–5 and 8. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding a polypeptide comprising any one of the amino acid sequences of SEQ ID NO: 1, SEQ ID NO: 2, SEQ ID NO: 3, SEQ ID NO: 4, SEQ ID NO: 5, SEQ ID NO: 8 and/or SEQ ID NO: 10, as used herein, include those with deletions, insertions, or substitutions of different nucleotides resulting in a polynucleotide that encodes the same or a functionally equivalent polypeptide. The encoded protein may also be "altered" and contain deletions, insertions, or substitutions of amino acid residues which produce a silent change and result in a functionally equivalent polypeptide.

"Amino acid sequence", as used herein, refers to an oligopeptide, peptide, polypeptide, or protein sequence, and fragment thereof, and to naturally occurring or synthetic molecules. Fragments of a polypeptide comprising any one of the amino acid sequences of SEQ ID NOs: 1–5 and 8 are preferably about 15 to about 30 amino acids in length and retain the biological activity or the immunological activity of the fall polypeptide.

"Amplification", as used herein, refers to the production of additional copies of a nucleic acid sequence and is generally carried out using polymerase chain reaction (PCR) technologies well known in the art (PCR Primer, a Laboratory Manual, Cold Spring Harbor Press, Plainview, N.Y.).

The term "antagonist", as used herein, refers to a molecule which, when bound to a polypeptide comprising any one of the amino acid sequences of SEQ ID NOs: 1–5 and 8, decreases the amount or the duration of the effect of the biological activity of polypeptide.

The term "agonist" as used herein, refers to a molecule which, when bound to a polypeptide comprising any one of the amino acid sequences of SEQ ID NOs: 1–5 and 8, increases or prolongs the effect of the polypeptide.

As used herein, the term "antibody" refers to intact molecules as well as fragments thereof, such as Fa, F(ab')$_2$ and Fv, which are capable of binding the epitopic determinant. Antibodies that bind a polypeptide comprising any one of the amino acid sequences of SEQ ID NOs: 1–5 and 8 can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "biologically active," as used herein, refers to a protein having structural, regulatory, or biochemical functions of a naturally occurring molecule. Likewise, "immunologically active" refers to the capability of the natural, recombinant, or synthetic polypeptide comprising any one of the amino acid sequences of SEQ ID NOs: 1–5 and 8, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding polypeptide comprising any one of the amino acid sequences of SEQ ID NOs: 1–5 and 8 may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

The term "correlates with expression of a polynucleotide", as used herein, indicates that the detection of the presence of ribonucleic acid that is similar to SEQ ID NO:6, SEQ ID NO:7, or SEQ ID NO:9 by northern analysis is indicative of the presence of mRNA encoding a polypeptide comprising any one of the amino acid sequences of SEQ ID NOs: 1–5 and 8 or a homologous amino acid sequence with at least 60% homology and thereby correlates with expression of the transcript from the polynucleotide encoding the protein.

A "deletion", as used herein, refers to a change in the amino acid or nucleotide sequence and results in the absence of one or more amino acid residues or nucleotides.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides arranged on a substrate, such as paper, nylon or other type of membrane, filter, chip, glass slide, or any other suitable solid support.

The term "modulate", as used herein, refers to a change in the activity of a polypeptide comprising any one of the amino acid sequences of SEQ ID NOs: 1–5 and 8. For example, modulation may cause an increase or a decrease in protein activity, binding characteristics, or any other biological, functional or immunological properties of the polypeptide.

"Nucleic acid sequence" as used herein refers to an oligonucleotide, nucleotide, or polynucleotide, and to DNA or RNA of genomic or synthetic origin which may be single- or double-stranded, and represent the sense or antisense strand.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

The term "purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of a polypeptide comprising any one of the amino acid sequences of SEQ ID NOs: 1–5, 8 and 10, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

II. Polynucleotide

A. Isolated and Purified Polynucleotides

In one aspect, the present invention provides for an isolated and purified polynucleotide sequence selected from the group consisting of SEQ ID NO: 6, SEQ ID NO: 7 and SEQ ID NO: 9. Additionally, the polynucleotides of the present invention may encode for a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10.

As used herein, the term "polynucleotide" means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

The invention also encompasses a variant of a polynucleotide sequence encoding a polypeptide comprising an amino acid sequence selected from the group consisting of SEQ ID NO: 1, SEQ ED NO: 2, SEQ ID NO: 3, SEQ ID NO: 4, SEQ ID NO: 5, SEQ ID NO: 8 and/or SEQ ID NO: 10. In particular, such a variant polynucleotide sequence will have at least about 80%, more preferably at least about 90%, and most preferably at least about 95% polynucleotide sequence identity to a polynucleotide sequence encoding a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10.

A polynucleotide of the present invention can be prepared using standard techniques well known to one of skill in the art. The preparation of a cDNA molecule encoding a peptide of the present invention is described hereinafter. A polynucleotide can also be prepared from genomic DNA libraries using lambda phage technologies.

In another aspect, the present invention provides an isolated and purified polynucleotide that encodes a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10, where the polynucleotide is preparable by a process comprising the steps of constructing a library of cDNA clones from a cell that expresses the polypeptide; screening the library with a labeled cDNA probe prepared from RNA that encodes the polypeptide; and selecting a clone that hybridizes to the probe.

B. Probes and Primers

In another aspect, DNA sequence information provided by the present invention allows for the preparation of relatively short DNA (or RNA) sequence having the ability to specifically hybridize to gene sequences of the selected polynucleotide disclosed herein. In these aspects, nucleic acid probes of an appropriate length are prepared based on a consideration of a selected nucleotide sequence. The ability of such nucleic acid probes to specifically hybridize to a polynucleotide encoding a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 lends them particular utility in a variety of embodiments. Most importantly, the probes can be used in a variety of assays for detecting the presence of complementary sequences in a given sample.

To provide certain of the advantages in accordance with the present invention, a preferred nucleic acid sequence employed for hybridization studies or assays includes probe molecules that are complementary to at least a 10 to 70 or so long nucleotide stretch of a polynucleotide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 55. Such fragments can be readily prepared by, for example, directly synthesizing the fragment by chemical means, by application of nucleic acid reproduction technology, such as the PCR or by excising selected DNA fragments from recombinant plasmids containing appropriate inserts and suitable restriction enzyme sites.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02M–0.15M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate a peptide coding sequence from other cells, functional equivalents, or the like, less stringent hybridization conditions are typically needed to allow formation of the heteroduplex. In these circumstances, one can desire to employ conditions such as 0.15M–0.9M salt, at temperatures ranging from 20° C. to 70° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C content, type of target nucleic acid, source of nucleic acid, size of hybridization probe). Following washing of the matrix to remove non-specifically bound probe molecules, specific hybridization is detected, or even quantified, by means of the label.

III. Peptides and Gene Transcription Regulatory Peptide

In one embodiment, the present invention contemplates an isolated and purified peptide that modulates programmed cell death. Preferably, the peptide that modulates programmed cell death has at least 60% homology to a peptide comprising an amino acid sequence of SEQ ID NO: 1 including at least one amino acid sequence selected from the group consisting of SEQ ID NO: 2, SEQ ID NO: 3, SEQ ID NO: 4, SEQ ID NO: 5, SEQ ID NO: 8 and/or SEQ ID NO: 10.

The invention also encompasses peptide variants. A preferred variant is one which has at least about 80%, more preferably at least about 90%, and most preferably at least about 95% amino acid sequence identity to the amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10, and which modulates programmed cell death.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like peptide characteristics that modulate programmed cell death. For example, certain amino acids can be substituted for other amino acids in a sequence without appreciable loss of peptide activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte, J. and R. F. Doolittle 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of a peptide as set forth above.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed.

In general, the technique of site-specific mutagenesis is well known in the art. As will be appreciated, the technique typically employs a phage vector which can exist in both a single stranded and double stranded form. Typical vectors useful in site-directed mutagenesis include vectors such as the M13 phage. These phage are commercially available and their use is generally known to those of skill in the art.

In general, site-directed mutagenesis in accordance herewith is performed by first obtaining a single-stranded vector which includes within its sequence a nucleotide sequence which encodes all or a portion of the peptide sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10. An oligonucleotide primer bearing the desired mutated sequence is prepared, generally synthetically, by methods well known in the art. This primer is then annealed to the singled-stranded vector, and extended by the use of enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells.

IV. Expression Vectors

In another embodiment, the present invention provides expression vectors comprising polynucleotides that encode for modulating peptides of programmed cell death. Preferably, expression vectors of the present invention comprise polynucleotides that encode polypeptides comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10. The expression vector can include the peptide coding region itself of any of the above sequences or it can contain coding regions bearing selected alterations or modifications in the basic coding region of such peptides. Alternatively, such vectors or fragments can code larger polypeptides or peptides which nevertheless include the basic coding region. In any event, it should be appreciated that due to codon redundancy as well as biological functional equivalence, this aspect of the invention is not limited to the particular DNA molecules corresponding to the polypeptide sequences noted above.

The expression vectors of the present invention preferably comprise polynucleotides operatively linked to an enhancer-promoter. More preferably still, expression vectors of the invention comprise a polynucleotide operatively linked to a prokaryotic or eukaryotic promoter.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promote" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized. A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region is derived from a bovine growth hormone gene.

Exemplary vectors include the mammalian expression vectors of the pCMV family including pCMV6b and pCMV6c (Chiron Corp., Emeryville Calif.) and pRc/CMV (Invitrogen, San Diego, Calif.). In certain cases, and specifically in the case of these individual mammalian expression vectors, the resulting constructs can require co-transfection with a vector containing a selectable marker such as pSV2neo.

Where expression of recombinant polypeptide of the present invention is desired and a eukaryotic host is contemplated, it is most desirable to employ a vector, such as a plasmid, that incorporates a eukaryotic origin of replication. Additionally, for the purposes of expression in eukaryotic systems, one desires to position the desired peptide encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit, an appropriate polyadenylation site.

The pRc/CMV vector (available from Invitrogen) is an exemplary vector for expressing a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 in mammalian cells, particularly COS, CHO, human MCF-F, human 293T and BHK bovine cells. A polypeptide of the present invention under the control of a CMV promoter can be efficiently expressed in mammalian cells. The pCMV plasmids are a series of mammalian expression vectors of particular utility in the present invention. The vectors are designed for use in essentially all cultured cells and have been successfully expressed in simian COS cells, mouse L cells, CHO cells, and HeLa cells.

V. Transfected Cells

In yet another embodiment, the present invention provides recombinant host cells transformed or transfected with a polynucleotide that encodes a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10, as well as transgenic cells derived from those transformed or transfected cells. Means of transforming or transfecting cells with exogenous polynucleotide such as DNA molecules are well known in the art and include techniques such as calcium-phosphate-or DEAE-dextran-mediated transfection, protoplast fusion, electroporation, liposome mediated transfection, direct microinjection and adenovirus infection.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured marumalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA or RNA within liposomes, followed by fusion of the liposomes with the cell membrane. The mechanism of how nucleotides is delivered into the cell is unclear but transfection efficiencies can be as high as 90%.

A transfected cell can be prokaryotic or eukaryotic. In general, prokaryotes are preferred for the initial cloning of nucleotides sequences and constructing the vectors useful in the invention. For example, E. coli K12 strains can be particularly useful. Other microbial strains which can be used include E. coli B, and E. coli X1776 (ATCC No. 31537). These examples are, of course, intended to be illustrative rather than limiting.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli can be transformed using pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems and a tryptophan (TRP) promoter system. While these are the most commonly used, other microbial promoters have been discovered and utilized, and details concerning their nucleotide sequences have been published, enabling a skilled worker to introduce functional promoters into plasmid vectors.

In addition to prokaryotes, eukaryotic microbes, such as yeast can also be used. Saccharomyces cerevisiae or common baker's yeast is the most commonly used among eukaryotic microorganisms, although a number of other strains are commonly available. For expression in Saccharomyces, the plasmid YRp7, for example, is commonly used. This plasmid already contains the trp1 gene which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan. Suitable promoter sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination.

Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20, VERO and HeLa cells, Chinese hamster ovary (CHO) cell lines, and W138, BHK, COSM6, COS-1, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication. Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

VI. Preparation of Polypeptides

In yet another embodiment, the present invention contemplates a process of preparing a programmed cell death modulating peptide comprising transfecting cells with a polynucleotide that encodes a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 to produce transformed host cells; and maintaining the transformed host cells under biological conditions sufficient for expression of the polypeptide. Preferably, the transformed host cells are eukaryotic cells. Alternatively, the host cells are prokaryotic cells.

A host cell used in the process is capable of expressing a functional, recombinant peptide of the present invention. A variety of cells are amenable to a process of the invention, for instance, yeasts cells, human cell lines, and other eukaryotic cell lines well known to those of the art.

Following transfection, the cell is maintained under culture conditions for a period of time sufficient for expression of a peptide. Culture conditions are well known in the art and include ionic composition and concentration, temperature, pH and the like. Suitable medium for various cell types are well known in the art. In a preferred embodiment, temperature is from about 20° C. to about 50° C. pH is preferably from about a value of 6.0 to a value of about 8.0. Other biological conditions needed for transfection and expression of an encoded protein are well known in the art.

Transfected cells are maintained for a period of time sufficient for expression of the desired peptide. A suitable time depends inter alia upon the cell type used and is readily determinable by a skilled artisan. Typically, maintenance time is from about 2 to about 14 days.

A recombinant peptide having the ability to modulate programmed cell death is recovered or collected either from the transfected cells or the medium in which the cells are cultured. Recovery comprises isolating and purifying the recombinant polypeptide. Isolation and purification techniques for polypeptides are well known in the art and include such procedures as precipitation, filtration, chromatography, electrophoresis and the like.

VII. Antibodies

In still another embodiment, the present invention provides antibodies immunoreactive with a polypeptide of the present invention. The antibodies may include both monoclonal and polyclonal immunoreactive with a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10. Means for preparing and characterizing antibodies are well known in the art.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide may vary in its immunogenicity. It is often necessary therefore to couple the immunogen (e.g., a polypeptide of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, M maleimidobenzoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various points following immunization. When a desired level of immunogenicity is obtained, the immunized animal can be bled and the serum isolated and stored.

Typically, a monoclonal antibody of the present invention can be readily prepared by a technique which involves first immunizing a suitable animal with a selected antigen (e.g., a polypeptide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine. This culturing provides a population of hybridomas from which specific hybridomas are selected. Typically, selection of hybridomas is performed by culturing the cells by single-clone dilution in microliter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed Mycobacterium tuberculosis). At some time (e.g., at least two weeks) after the first injection, mice are boosted by injection with a second dose of the antigen mixed with incomplete Freund's adjuvant. A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigenpolypeptide of the present invention. Fusion conditions include, for example, the presence of polyethylene glycol. The resulting fused cells are hybridoma cells. Like myeloma cells, hybridoma cells grow indefinitely in culture. Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media. Each of the surviving hybridoma cells produces a single antibody. These cells are then screened for the production of the specific antibody immunoreactive with an antigenpolypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides of the invention can be recognized as antigens, and thus identified. Once identified, those polypeptides can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide is then easily removed from the substrate and purified.

VIII. Pharmaceutical Compositions

In a preferred embodiment, the present invention provides pharmaceutical compositions comprising a programmed cell death modulating peptide and a physiologically acceptable carrier. More preferably, a pharmaceutical composition comprises a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intravascularly).

IX. Screening Assays

In yet another aspect, the present invention contemplates a process of screening substances for their ability to interact with a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10, the process comprising the steps of providing a polypeptide of the present invention and testing the ability of selected test substances to interact with that polypeptide.

The methods of the present invention make it possible to produce large quantities of a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 for use in screening assays. More important, however, is the relative purity of the peptides provided by the present invention. A relatively pure peptide preparation for assaying a protein-protein interaction makes it possible to use elutive methods without invoking competing, and unwanted, side-reactions.

Screening assays of the present invention generally involve determining the ability of a candidate test substance to bind to the polypeptides of the present invention. The peptides of the present invention can be coupled to a solid support. The solid support can be agarose beads, polyacrylamide beads, polyacrylic beads or other solid matrices capable of being coupled to proteins. Well known coupling agents include cyanogen bromide, carbonyidiimidazole, tosyl chloride, and glutaraldebyde.

X. Therapeutics

In cancers where there is an increase in cell proliferation, it may be is desirable to increase the expression of a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 to limit cell proliferation. Therefore, in one embodiment, a programmed cell death modulating peptide may be administered to a subject to prevent or treat cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In disorders associated with an increase in cell death or apoptosis it may be desirable to decrease the activity of the peptides of the present invention by administering an antagonist of a polypeptide comprising an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 to stimulate cell proliferation. In particular, the antagonist may be added to a cell or cells in vivo using delivery mechanisms such as liposomes, viral based vectors, or electroinjection for the purpose of promoting regeneration or cell differentiation of the cell. Diseases include AIDS and other infectious or genetic immunodeficiencies; neurodegenerative diseases, such as Alzheimer's disease, Parkinson's disease, amyotrophic lateral sclerosis, retinitis pigmentosa, and cerebellar degeneration; myelodysplastic syndromes, such as aplastic anemia; ischemic injuries, such as myocardial infarction, stroke, and reperfusion injury; toxin-induced diseases, such as alcohol-induced liver damage, cirrhosis, and lathyrism; wasting diseases, such as cachexia; viral infections, such as those caused by hepatitis B and C, and osteoporosis.

An antagonist of the polypeptides of the present invention which comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 8 and/or SEQ ID NO: 10 may be produced using methods which are generally known in the art. In particular, polypeptides of the present invention may be used to produce antibodies or to screen libraries of pharmaceutical agents to identify those which specifically bind to these polypeptides of the present invention and reduce their apoptopic activity.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

It is understood that modification that do not substantially affect the activity of the various embodiments of this invention are also included within the definition of the invention provided herein. Accordingly, the following examples are intended to illustrate but not limit the present invention.

EXAMPLE 1

Tissue Distribution

For further characterization of the hE93 A and B genes, analysis of tissue distribution was performed. This analysis was performed by RNA blot analysis with RNA isolated from human tissue. Briefly, tissue distribution of hE93 mRNA was performed on northern blots prepared and obtained from Origene, Inc. Radioactive hE93 probe was prepared and the blots were hybridized with the common region of the hE93 A and B transcription units, washed and then visualized by autoradiography.

Figure 5:
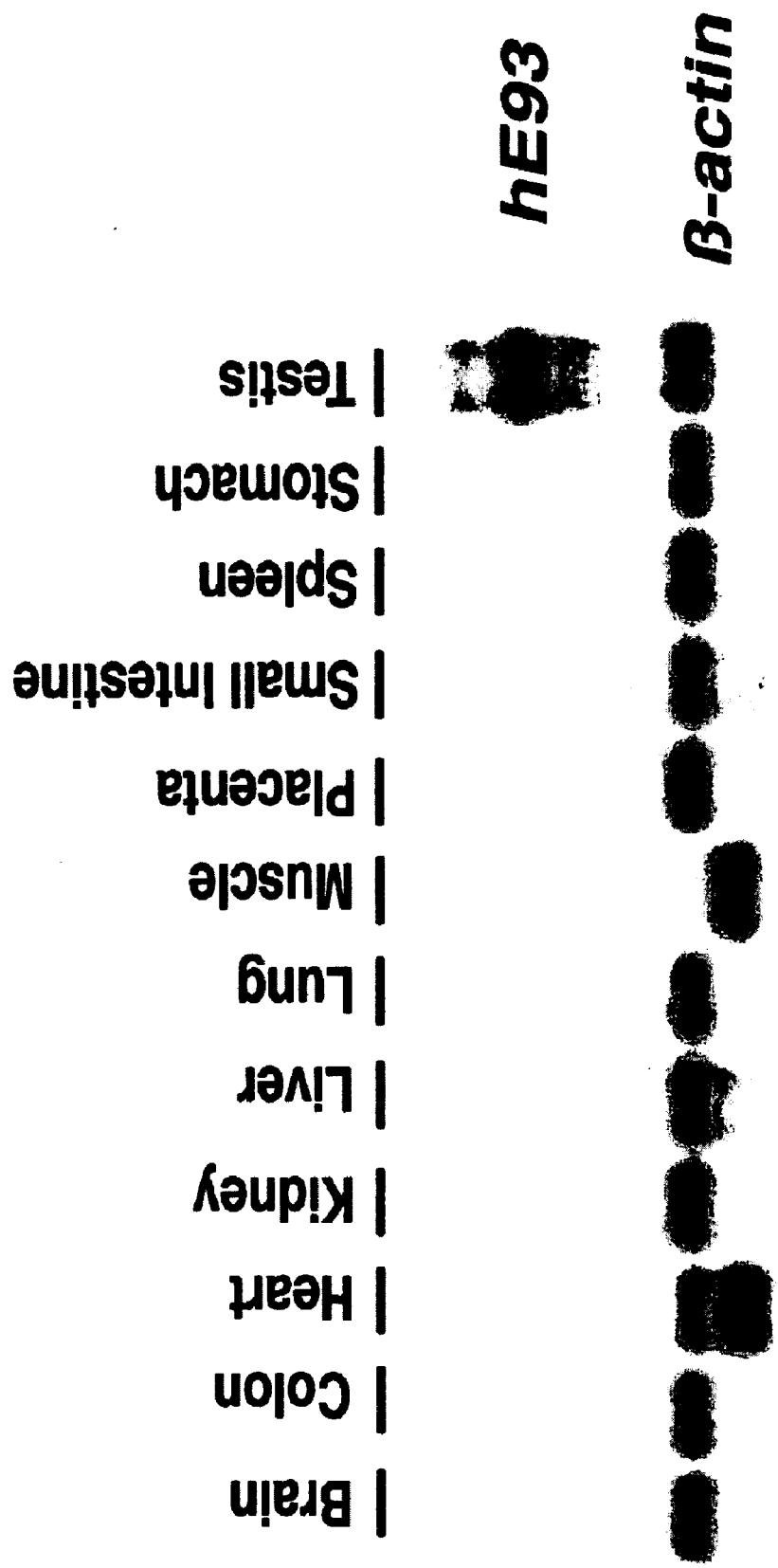
FIG. 5 shows Northern blot hybridization analyses of human E93 transcription in different tissues. Human E93 transcripts were detected in brain, kidney, muscle, small intestine, and testis.

It was found that hE93 is transcribed at high levels in testis, and lower levels in brain, kidney, muscle, and small intestine, as shown in FIG. 5. Two transcripts were detected that were approximately 5.0 and 7.0 kilobases in length. The smaller 5.0 kilobase transcript, found to be very abundant in testis, is similar in size to the cDNA that was isolated from a testis cDNA library, indicating that we have characterized a full length or nearly full length gene. While the 6074 base cDNA that was isolated from the brain library is smaller than the large transcript detected by northern blot hybridization, this cDNA has multiple stop codons in all three reading frames upstream of the start AUG codon that is shared by both cDNAs, indicating the identification of the full length hE93 protein.

EXAMPLE 2

Expression of hE93 is Sufficient to Induce Programmed Cell Death in Human Cells

The open reading region of the hE93 gene was placed into a tissue culture cell transfection vector such that hE93 would be expressed in cells to test if expression of the hE93 expressed protein is sufficient to induce programmed cell death. As controls, cells were transfected with an empty vector, the same vector except that it contains either: (1) green fluorescent protein (GFP) which is used to monitor transfection rate, (2) the proapoptotic protein Bax which is sufficient to induce programmed cell death (Adams and Cory, 1998), (3) the antiapoptotic protein Bcl-xl (Adams and Cory, 1998). Each of these gene constructs were transfected into equal numbers of Bovine BHK, human MCF-7, and human 293T cell lines. Nineteen hours post transfection the cell viability was assayed (Table 1). The empty vector and GFP constructs did not significantly impact cell viability. In contrast, expression of Bax significantly reduced the viability of all 3 cell lines as has been previously demonstrated for this proapoptotic protein. The antiapoptotic protein Bcl-xl had some impact on the viability of BHK and 293T cells. Interestingly, hE93 protein expression was the most potent inducer of cell death in the human MCF-7 and 293T cell lines, but did not induce significant levels of cell death in the bovine cells. This specificity is very unique. The data indicate that expression of the hE93 gene is sufficient to induce apoptosis.

TABLE 1

Percent cell viability when cell lines are transformed with expression constructs
TRANSFORMATION CONSTRUCTS

| cell line | empty vector | GFP | BAX | Bcl-x1 | hE93 |
|---|---|---|---|---|---|
| BHK | 98 | 92 | 32 | 55 | 72 |
| MCF-7 | 97 | 94 | 7 | 105 | 2 |
| 293-T | 98 | 90 | 21 | 75 | 4 |

REFERENCES

All publications mentioned herein are incorporated herein by reference for the all purposes.

Adams, J. M., and Cory, S. (1998). The Bcl-2 protein family arbiter of cell survival. Science 281, 1322–1326.

Baehrecke, E. H. and Thummel, C. S. (1995). The *Drosophila* E93 gene from the 93F early puff display stage and tissue specific regulation by 20-hydroxyecdysone. Dev. Biol. 171, 85–97.

Cyrns, V., and Yuan, J., (1998). Proteases to die for. Genes Dev. 12, 1551–1570.

Ellis, R. E., et al. (1991). Mechanisms and functions of cell death. Annu. Rev. Cell Bio., 7:663–698

Haining, W. N., Carboy-Newcomb, C., Wei, C. L., and Steller, H. (1999). The proapoptotic function of Drosophilia Hid is conserved in mammalian cell. Proc. Natl. Acad. Sci. USA 96, 4936–4941.

Lee, C. Y., and Baehrecke, E. H. (2001). Steroid regulation of autophagic programmed cell death during development. 128, 1443–1455.

Lee, C. Y., Wendel, D. P., Reid, P., Lam G., Thummel, C. S. and Baehrecke, E. H. (2000). E93 directs steroid triggered programmed cell death in *Drosophila* . Mol. Cell 6, 433–443.

McCarthy, J. C. and Dixit, V. M. (1998) Apoptosis induced by *Drosophila* Reaper and Grim in a human system. J. Biol. Chem. 273, 24009–24015.

What is claimed is:

1. An isolated polypeptide that induces cell death in vitro, consisting of SEQ ID NO: 8.
2. A composition comprising an isolated polypeptide as of claim 1 and a carrier.
3. A method of generating an antibody, comprising:
   (a) introducing an isolated polypeptide of claim 1 into an immunocompetent animal in an amount sufficient to induce an immune response; and
   (b) recovering from serum of the immunocompetent animal antibodies generated in response to the polypeptide of step (a) and that bind therewith.
4. An isolated polypeptide that induces cell death in vitro comprising SEQ ID NO: 8.
5. A composition comprising an isolated polypeptide as of claim 4 and a carrier.

* * * * *